United States Patent [19]

Robinson et al.

[11] Patent Number: 5,423,738
[45] Date of Patent: Jun. 13, 1995

[54] BLOOD PUMPING AND PROCESSING SYSTEM

[76] Inventors: Thomas C. Robinson, 1040 Mariposa Ave., Berkeley, Calif. 94707; Sotiris Kitrilakis, 1520 Grand Ave., Piedmont, Calif. 94611; Timothy Appleby, 105 Willesden Dr., Cary, N.C. 27513; Thomas P. Sahines, 2023 Wellington Dr., Milpitas, Calif. 95035; Augustus Felix, 242 Roger Williams Ave., Providence, R.I. 02907; Klaus J. Cross, 8 Annisquam Heights, Gloucester, Mass. 01930; Craig Nevers, 37 Harold St., Warwick, R.I. 02888

[21] Appl. No.: 117,921

[22] Filed: Sep. 7, 1993

Related U.S. Application Data

[63] Continuation-in-part of Ser. No. 852,940, Mar. 13, 1992, Pat. No. 5,242,384.

[51] Int. Cl.⁶ .............................................. A61M 1/34
[52] U.S. Cl. ............................................ 604/4; 604/28; 604/48; 604/49
[58] Field of Search ................................. 604/4–6, 604/27, 28, 30, 31, 48, 49, 51, 52, 56, 118–120

[56] References Cited

U.S. PATENT DOCUMENTS

| | | |
|---|---|---|
| Re. 31,688 | 9/1984 | Popovich et al. |
| 2,664,085 | 12/1953 | Ryan et al. |
| 2,689,565 | 9/1954 | Gobel . |
| 2,812,716 | 11/1957 | Gray . |
| 2,954,738 | 10/1960 | DiVette . |
| 3,021,841 | 2/1962 | Burke . |
| 3,035,575 | 5/1962 | Broman . |
| 3,052,238 | 9/1962 | Broman et al. |
| 3,204,631 | 9/1965 | Fields . |
| 3,489,145 | 1/1970 | Judson et al. |
| 3,559,644 | 2/1971 | Stoft et al. |
| 3,572,979 | 3/1971 | Morton . |
| 3,579,441 | 5/1971 | Brown . |
| 3,655,123 | 4/1972 | Judson et al. |
| 3,791,767 | 2/1974 | Shill . |
| 3,811,800 | 5/1974 | Shill . |
| 3,814,547 | 6/1974 | Kitrilakis et al. |
| 3,890,969 | 6/1975 | Fischel . |
| 3,896,733 | 7/1975 | Rosenberg . |
| 3,964,484 | 6/1976 | Reynolds et al. |

(List continued on next page.)

FOREIGN PATENT DOCUMENTS

| | | |
|---|---|---|
| 0094682 | 5/1983 | European Pat. Off. . |
| 0303765 | 2/1989 | European Pat. Off. . |
| WO83/00020 | 1/1983 | WIPO . |

(List continued on next page.)

OTHER PUBLICATIONS

Klebanoff et al., "A Disposable Autotransfusion Unit", The American Journal of Surgery, vol. 116, p. 475 (Sep. 1968).

Tamura et al., "Therapeutic Practices in Plasmapheresis", Excerpta Medica, pp. 70–77, Amsterdam, 1985.

*Primary Exam*
*Attorney, Agent, or Firm*—Wolf, Greenfield & Sacks

[57] ABSTRACT

A blood processing system is described in which blood pressure readings obtained before and after passage of blood aspirated from an operative site through a membrane separator is used by a programmed controller to determine the hematocrit level of the blood and to add saline solution to adjust the hematocrit level to a desired level. The blood processing system contains a distributor cap to distribute wash solution to the inside of a filter to wash out additional blood cellular material within the filter. A precollector may be used remotely from the site of the blood processing system and later joined with the system to withdraw blood contained in the precollector for processing by the blood processing system.

28 Claims, 26 Drawing Sheets

U.S. PATENT DOCUMENTS

| | | |
|---|---|---|
| 3,965,896 | 6/1976 | Swank . |
| 3,974,825 | 8/1976 | Normann . |
| 3,993,067 | 11/1976 | Schachet et al. . |
| 4,014,329 | 3/1977 | Welch et al. . |
| 4,023,468 | 5/1977 | Poirier . |
| 4,043,501 | 8/1977 | Larrabee et al. . |
| 4,047,844 | 9/1977 | Robinson . |
| 4,152,786 | 5/1979 | Clark et al. . |
| 4,222,127 | 9/1980 | Donachy et al. . |
| 4,223,672 | 9/1980 | Terman et al. . |
| 4,243,530 | 1/1981 | Lehnhoff et al. . |
| 4,416,280 | 11/1983 | Carpenter et al. . |
| 4,424,053 | 1/1984 | Kurtz . |
| 4,443,220 | 4/1984 | Hauer et al. . |
| 4,445,884 | 5/1984 | Kurtz . |
| 4,479,760 | 10/1984 | Bilstad et al. . |
| 4,479,761 | 10/1984 | Bilstad et al. . |
| 4,500,308 | 2/1985 | Kurtz et al. . |
| 4,501,581 | 2/1985 | Kurtz et al. . |
| 4,540,406 | 9/1985 | Miles . |
| 4,540,413 | 9/1985 | Russo . |
| 4,540,506 | 9/1985 | Jacobson et al. . |
| 4,547,186 | 10/1985 | Bartlett . |
| 4,551,131 | 11/1985 | Miles . |
| 4,552,552 | 11/1985 | Polaschegg et al. . |
| 4,564,359 | 1/1986 | Ruhland . |
| 4,573,883 | 3/1986 | Noon et al. . |
| 4,573,992 | 3/1986 | Marx . |
| 4,619,639 | 10/1986 | Nose et al. . |
| 4,631,050 | 12/1986 | Reed et al. . |
| 4,634,430 | 1/1987 | Polaschegg . |
| 4,648,866 | 3/1987 | Malbrancq et al. . |
| 4,655,740 | 4/1987 | Ruhland . |
| 4,702,829 | 10/1987 | Polaschegg et al. . |
| 4,707,335 | 11/1987 | Fentress et al. . |
| 4,713,171 | 12/1987 | Polaschegg . |
| 4,713,176 | 12/1987 | Shoendorfer et al. . |
| 4,772,256 | 9/1988 | Lane et al. . |
| 4,775,360 | 10/1988 | Lane et al. . |
| 4,775,482 | 10/1988 | Thurman . |
| 4,828,543 | 4/1989 | Weiss et al. . |
| 4,850,995 | 7/1989 | Tie et al. . |
| 4,850,998 | 7/1989 | Schoendorfer . |
| 4,895,558 | 1/1990 | Cham . |
| 4,897,185 | 1/1990 | Schuyler et al. . |
| 4,911,703 | 3/1990 | Lysaght et al. . |
| 4,923,439 | 5/1990 | Seidel et al. . |
| 4,935,002 | 6/1990 | Gordon . |
| 4,954,128 | 9/1990 | Ford . |
| 4,964,847 | 10/1990 | Prince . |
| 4,981,596 | 1/1991 | Shiino et al. . |
| 5,004,458 | 4/1991 | Richalley et al. . |
| 5,034,188 | 7/1991 | Nakanishi et al. . |
| 5,098,372 | 3/1992 | Jonsson . |
| 5,295,953 | 3/1994 | Richard et al. .......... 604/5 |

OTHER PUBLICATIONS

Yamazaki, Z. "Therapeutic Practices in Plasmapheresis", Excerpta Medica, pp. 78–87, Amsterdam, 1985.

Sharp, M.D., W. V. et al., "Modern Operative Techniques: Modern Autotransfusion—Experience With A Washed Red Cell Processing Technique", The American Journal of Surgery, vol. 142 (Oct. 1981).

Mielke et al., "Technical and Therapeutic Applications of Plasma Exchange", Apheresis: Development, Applications and Collection.

Stummvoll, M. D. et al., "Spontaneous Aerteriovenous Plasma Separation", Critical Care Medicine, vol. 11(10) (1983).

Ottesen, S. et al., "Use of Haemonetics Cell Savor For Autotransfusion in Cardiovascular Surgery", Scan. J. Thor. Cadiovas. Surg., vol. 16, pp. 263–268 (1982).

Tretzel et al., "Computer Simulation of Cascade Filtration Procedures", Plasma Separation and Plasma Fractionation, pp. 235–244 (1983).

Callegaro, L. et al., "The Use of Hollow Fiber Bioreactors for Blood and Plasma Purification", Plasma Separation and Plasma.

Pourrat et al., "On–Line Plasma Reprocessing by Convective Blood and Plasma Purification", Plasma Separation and Plasma Electrophoresis, Plasma Separation and Plasma Fractionation, pp. 303–311 (1983).

Lysaght et al., "Contemporary Technical Issues in Membrane Plasmapheresis: Controversies and Reconciliation", Plamsa Separation and Plasma Fractionation, pp. 315–328 (1983).

"Cell Saver: Autologous Blood Recovery System", Haemonetics Corp. Brochure, 1984.

(List continued on next page.)

OTHER PUBLICATIONS

"The Cell-Saver and Autologous Transfusion. An Underutilized Resource In Vascular Surgery", The American Journal of Surgery, vol. 152 (Jul. 1986).

Wabeke et al., "An Automatic Penumatically Drive Autotransfusion System: A Hematologic Evaluation In Dogs", Surgery, vol. 99(3), p. 358 (Mar. 1986).

Kurtz, S. R. et al., "Evaluation of A Microporous Filtration Membrane System For Therpeutic Plasma Exchange", Vox Sang, vol. 53, pp. 89-95 (1987).

Castino et al., "Microemboli-Free Blood Detoxification Utilizing Plasma Filtration", Trans. Amer. Soc. Artif. Int. Organs, vol. 22, pp. 637-645 (1976).

Stairmand et al., "Separation of Plasma From Whole Blood By Membrane Filtration In Oscillatory Flows", Life Support Systems, No. 3, pp. 193-204, (Jul.-Sep./1986).

Tretzel et al., "Computer Simulation of Cascade Filtration Procedures", Plasma Separation and Plasma Fractionation, pp. 235-244.

Tamura et al., "Donor Plasmapheresis By The Membrane Method, Current Practice In Therapeutic Plasmapheresis", (1985).

Puratt et al., "On-Line Plasma Reprocessing By Convection Electrophoresis", Plasma Separation and Plasma Fractionation, pp. 303-311 (1983).

Nielke, Jr. et al., "Technical and Therapeutic Applications By Plasma Exchange", Apheresis: Developments and Collections Procedures, pp. 123-145, (1981).

Puratt et al., "On-Line Plasma Reprocessing By Convection Electrophoresis", Plasma Separation and Plasma Fractionation, pp. 303-311, (1983).

Callegaro et al., "The Use of Hollow Fiber Bioreactors For Blood and Plasma Purification", Plasma Separation and Plasma Fractionation, pp. 298-302 (1983).

SALINE PUMP EJECTION AIR FLOW RATE CONTROL

|      | S1 (X) | S2 (2X) | S3 (4X) | S4 (8X) | S5 (16X) |
|------|--------|---------|---------|---------|----------|
| x    | ON     |         |         |         |          |
| 2x   |        | ON      |         |         |          |
| 3x   | ON     | ON      |         |         |          |
| 4x   |        |         | ON      |         |          |
| 5x   | ON     |         | ON      |         |          |
| 6x   |        | ON      | ON      |         |          |
| 7x   | ON     | ON      | ON      |         |          |
| 8x   |        |         |         | ON      |          |
| 9x   | ON     |         |         | ON      |          |
| 10x  |        | ON      |         | ON      |          |
| 11x  | ON     | ON      |         | ON      |          |
| 12x  |        |         | ON      | ON      |          |
| 13x  | ON     |         | ON      | ON      |          |
| 14x  |        | ON      | ON      | ON      |          |
| 15x  | ON     | ON      | ON      | ON      |          |
| 16x  |        |         |         |         | ON       |
| 17x  | ON     |         |         |         | ON       |
| 18x  |        | ON      |         |         | ON       |
| 19x  | ON     | ON      |         |         | ON       |
| 20x  |        |         | ON      |         | ON       |
| 21x  | ON     |         | ON      |         | ON       |
| 22x  |        | ON      | ON      |         | ON       |
| 23x  | ON     | ON      | ON      |         | ON       |
| 24x  |        |         |         | ON      | ON       |
| 25x  | ON     |         |         | ON      | ON       |
| 26x  |        | ON      |         | ON      | ON       |
| 27x  | ON     | ON      |         | ON      | ON       |
| 28x  |        |         |         | ON      | ON       |
| 29x  | ON     |         | ON      | ON      | ON       |
| 30x  |        | ON      | ON      | ON      | ON       |
| 31x  | ON     | ON      | ON      | ON      | ON       |

Fig. 8d

SOFTWARE LOOK-UP TABLE
RELATING SALINE FLOW RATE TO FIRST SEPARATOR BLOOD PRESSURE DROP

| | | |
|---|---|---|
| ENTRY | 0 = | −10 |
| ENTRY | 1 = | −10 |
| ENTRY | 2 = | −10 |
| ENTRY | 3 = | −10 |
| ENTRY | 4 = | −10 |
| ENTRY | 5 = | 18 |
| ENTRY | 6 = | 25 |
| ENTRY | 7 = | 31 |
| ENTRY | 8 = | 39 |
| ENTRY | 9 = | 47 |
| ENTRY | 10 = | 54 |
| ENTRY | 11 = | 62 |
| ENTRY | 12 = | 71 |
| ENTRY | 13 = | 80 |
| ENTRY | 14 = | 89 |
| ENTRY | 15 = | 99 |
| ENTRY | 16 = | 108 |
| ENTRY | 17 = | 117 |
| ENTRY | 18 = | 124 |
| ENTRY | 19 = | 131 |
| ENTRY | 20 = | 138 |
| ENTRY | 21 = | 145 |
| ENTRY | 22 = | 151 |
| ENTRY | 23 = | 156 |
| ENTRY | 24 = | 160 |
| ENTRY | 25 = | 163 |
| ENTRY | 26 = | 166 |
| ENTRY | 27 = | 169 |
| ENTRY | 28 = | 172 |
| ENTRY | 29 = | 175 |
| ENTRY | 30 = | 178 |
| ENTRY | 31 = | 181 |

ENTRY X = PRESSURE DROP

Fig. 8e

BLOOD PUMPING AND PROCESSING SYSTEM

FIELD OF INVENTION

The present application is a continuation-in-part of application Ser. No. 07/852,940, filed Mar. 13, 1992, now U.S. Pat. No. 5,242,384, issued Sep. 7, 1993. The invention relates to a pumping apparatus and method for use in the processing of blood. Blood can be filtered and undesirable substances removed, other substances can be added, or the blood can be otherwise treated and then administered to a patient, for example, during a surgical procedure.

BACKGROUND OF THE INVENTION

The pumping and processing of blood has been routinely performed with patients as a means of processing their own blood or blood taken from another person and administered to the patient. Blood processing can be performed to remove a variety of blood constituents for therapeutic purposes. Hemodialysis is a widely used processing methodology that removes metabolic waste products from the blood of patients suffering from inadequate kidney function. Blood flowing from the patient travels across membranes which remove these waste products. The processed blood is then returned to the patient. Plasmapheresis similarly processes blood using tangential flow membrane separation to remove blood plasma constituents, such as cholesterol, to treat a wide variety of disease states. Membrane pore sizes are selected to remove the unwanted plasma constituents in a tangential or cross-flow separator. Hemoconcentrators use membranes with very small pores or non-porous membranes which permit water diffusion, to remove water or fluid with electrolytes from blood that is too dilute. Blood may similarly be processed in a device which utilizes biochemical reactions to modify biological constituents present in blood as a treatment for certain diseases. For example, enzymes can be bonded to membrane surfaces or gel immobilized and blood components such as bilirubin or phenols can be gluconized or sulfated by the in vitro circulation of blood plasma across these bonded enzyme surfaces. Blood is routinely processed by the addition of an anticoagulant to prevent its clotting while it is outside the body.

Blood may be processed during surgery to permit blood flowing from a wound or incision to be reinfused into the patient. This is called intraoperative autotransfusion. Such processing may include anti-coagulation and the removal of particles (debris from the wound site and clots) larger than red cells. This processing may include the removal of blood plasma and damaged blood tissue components (i.e., free plasma hemoglobin) and anticoagulant, with or without the addition of a saline washing fluid to aid in plasma removal and to replace some of the lost fluid.

Techniques and apparatus have been available for some time for washing blood cells prior to returning them to the patient. In such techniques a centrifuge is used for separating and washing the red cells in batches and they are resuspended in a balanced salt solution before infusion into the patient. This is a relatively slow process, the apparatus is complex and expensive and expertise is needed to run the apparatus.

More recently, as set forth in U.S. Pat. No. 4,631,050, issued to Charles C. Reed and Denton A. Cooley on Dec. 23, 1986, an autotransfusion system is utilized wherein the centrifuge is replaced by an ultrafiltration module. The apparatus utilizes a receiving chamber having a semipermeable membrane at least partially bonded to its inside surface. The chamber is pressurized so as to provide a significant pressure differential across the membrane and fluid and small particles are forced out of the blood and through the membrane while the membrane holds up the red cells. Thereafter, washing solution is injected into the receiving chamber to assist in plasma removal and the blood cells, along with some of the washing fluid, are swept out of the chamber and reinfused into the patient.

The system and method of U.S. Pat. No. 4,631,050 suffer from a number of problems. One of the problems is that a thick layer of red cells is formed and is retained above the ultrafiltration membrane. This requires that a relatively high pressure be provided across the membrane to achieve any practical plasma removal rate. This limits the speed of filtration. Also, the red cells held against the membrane can be damaged when subjected to the pressure differential whereby the proportion of undamaged red cells recovered and reinfused into the patient is limited. Further, the apparatus of U.S. Pat. No. 4,631,050 utilizes roller pumps which can themselves damage red cells thus still further reducing the proportion of red cells returnable to the patient. In addition, there is no means for mixing washing fluid and blood uniformly to obtain efficient washing. Also, washing fluid is added before any ultrafiltration which requires relatively large quantities of washing fluid for plasma removal. The apparatus of U.S. Pat. No. 4,631,050 only provides for batchwise addition of washing fluid rather than continuous 354 addition of washing fluid whereby washing is not as efficient as would be desired.

In plasmapheresis membrane tangential flow separators have been utilized to remove plasma from blood as an alternative to centrifugation. U.S. Pat. No. Re. 31,688 reissued Sep. 25, 1984 to R. P. Popovich, J. W. Moncrief and G. D. Antwiler discloses one such process. Such is also reported, for example, by M. Tamura and M. Kasai in Current Practice in Therapeutic Plasmapheresis, pp. 70-77, Edited by Y. Shiokawa and N. Inoue, Excerpta Medica, Amsterdam, 1985 as well as by Z. Yamazaki, et al., pp. 78-85, same book. Such membrane tangential flow separators have not, however, been known to be useful or been used in autotransfusion wherein very different problems are encountered. In plasmapheresis one has a consistent supply of whole blood, for example, from a blood vessel, and the blood flows at a relatively constant rate. In autotransfusion the rate of blood flow varies from zero on up to many times that which occurs in plasmapheresis and can do this several times intermittently during a surgical procedure. Also, it is not whole blood which flows but rather a mixture of fluids which include traumatized blood, clots, debris, entrapped gases, saline fluids, anticoagulant fluid and the like. Tangential flow separators are generally unable to handle such a mixture and would be damaged and/or clogged if one attempted to separate such a mixture using a plasmapheresis tangential separator apparatus.

The current systems for intraoperative autotransfusion, plasmapheresis, hemoconcentration, hemodialysis, and blood processing in general suffer from a number of problems. All are complex electromechanical systems which are expensive and require a trained operator as well as much time to set up and use. The systems are manual or semiautomatic but not automatic. They are not inherently safe but require sensors and safeguards and much attention to ensure safe operation. The processing of blood often occurs at rates lower than desired. The metering and mixing of anticoagulant with blood is often inadequate, leading to insufficient anti-coagulation and clotting or excessive anti-coagulation, higher cost for the anticoagulant, and the need to remove this excess (or all anticoagulant) before returning blood to the patient. Damage to retained blood constituents or excess removal of those which are desired to be retained often occurs with these systems. It is desired to retain close to 100% of the red cells and a significant proportion of platelets for return to the patient. Present systems retain substantially less than 100% of the red cells and a very low percentage of the original platelets.

The present invention is, in some of its embodiments, intended for use in all of the blood pumping and processing applications mentioned above, and in other embodiments, intended for use in autotransfusion, and is directed to overcoming one or more of the problems of existing devices as described herein.

DISCLOSURE OF THE INVENTION

In accordance with an embodiment of the invention particularly adapted for autotransfusion a blood pumping, filtering and separating apparatus is provided. A filter receives a mixture of blood cells, platelets, blood fluid and particulate matter and removes at least a portion of the particulate matter larger than blood cells, as well as any air contained in the mixture prior to the blood flowing to the pumping chamber. The filter has an outlet port from which the resulting filtered mixture exits. A main pump has a pumping chamber having a pump inlet port arranged to receive the filtered mixture and a pump outlet port from which the filtered mixture is pumped. Check valve means is located between the outlet port and the pump inlet port. It serves for preventing flow from the pumping chamber into the filter and for allowing flow from the filter outlet port to the pump inlet port when the filtered mixture is not being pumped out of the pump outlet port. A tangential flow separator has one or more narrow passages in parallel having a porous membrane having an infacing and an outfacing surface, and extending along the passage, the passage being no more than about 500 microns across. The passage extends from a separator inlet to a separator outlet. Delivery means serves for delivering the filtered mixture from the pumping chamber to the passage at a pressure in the passage sufficient to impel blood fluid through the porous membrane and at a flow rate through the passage sufficient to prevent the blood cells and platelets from blocking or passing through the porous membrane. Fluid removal means serves for removing blood fluid from the outfacing surface. A pressure adjacent the outfacing surface of the membrane is maintained less than the pressure in the passage.

In accordance with an additional embodiment of the invention useful in a number of blood processing operations a blood pumping and fluid introduction apparatus is set forth. The apparatus comprises a main pump having a pumping subchamber having a pump inlet port arranged to receive blood and a pump outlet port from which said blood is pumped, the main pump having a substantially biconcave main pump chamber divided by a main pump diaphragm into the pumping subchamber and a pressurization subchamber. A blood delivery system is present for delivering blood to the pump inlet port. Valve means is present between the blood delivery system and the pump inlet port for (1) preventing flow from the pumping subchamber back into the blood delivery system and for (2) allowing flow from the blood delivery system to the pump inlet port when blood is not being pumped out of The pump outlet port. Means is present for determining when the main pump pumping subchamber is substantially full. Main pump pressurizing means is present for pressurizing the main pump pressurization subchamber, in response to the main pump pumping subchamber being substantially full, sufficiently to impel substantially all of the blood out of the pump outlet port. A fluid introduction pump is positioned to deliver a fluid to the blood. Means is present for respectively starting and stopping the fluid introduction pump in response respectively to starting and stopping of pumping of the main pump.

In accordance with another embodiment of the present invention useful in a number of blood processing operations a blood pumping and processing apparatus is disclosed. The apparatus comprises a rigid main pump housing having an internal wall structure, the main pump diaphragm dividing the chamber into a pressurization subchamber and a stroking subchamber. The diaphragm is of a shape and size sufficient to fit substantially matingly against the internal wall structure defining each of the subchambers whereby by diaphragm motion and flexing each of said subchambers can vary in size from substantially zero volume to substantially the volume of said chamber. Inlet valve means is present for delivering blood to said stroking chamber and for preventing backflow. Outlet valve means is present for permitting blood to leave the stroking chamber and for preventing backflow. Means is present for controlling the rate of flow of blood out of the stroking chamber. Means is present for pressurizing the pressurization subchamber at a controlled rate sufficiently to motivate the diaphragm to substantially matingly fit against the internal wall structure defining the stroking chamber to expel substantially all blood in the stroking subchamber through the outlet valve means. Means is present for depressurizing the pressurization subchamber at a controlled rate sufficiently to motivate said diaphragm to substantially matingly fit against the internal wall structure defining the pressurization subchamber. Means is present for sensing when the stroking subchamber is substantially full and for activating the pressurizing means when the stroking subchamber is substantially full. Means is also present for processing blood flowing to or from the main pump.

In accordance with yet another embodiment of the present invention particularly adapted for autotransfusion a method is set forth of separating blood cells from blood plasma. A mixture of healthy blood cells, platelets, plasma, particulate matter and entrapped gases is filtered and defoamed to remove at least a portion of the particulate matter and at least a portion of the entrapped gases to form a defoamed and filtered mixture. The defoamed and filtered mixture is pumped through a tangential flow separator having one or more narrow passages in parallel having a porous membrane having an infacing surface and an outfacing surface and extending along the passage, the passage being no more than about 500 microns across. The passage extends from a separator inlet to a separator outlet. The filtered mixture from the pumping chamber is delivered to the passage at a pressure in the passage sufficient to impel plasma through the porous membrane and at a flow rate through the passage sufficient to prevent the blood cells and platelets from blocking or passing through the porous membrane. Plasma is removed from the outfacing surface of the membrane by maintaining a pressure adjacent the outfacing surface of the membrane as less than that in the passage.

The apparatus and method in accordance with certain embodiments of the present invention operate with a relatively low pressure differential across the membrane in the tangential flow separator, when such is present. The red cells and platelets are not held by the membrane but, instead, are constantly stirred up and flowing along the membrane. This hydrodynamically prevents deposition of cells on to the membrane and concurrent blocking of the pores of the membrane when the membrane pores are smaller than the cells and platelets and hydrodynamically prevents the cells from passing through the membrane when the membrane pores are larger than the cells and platelets. The velocity of the plasma plus red cells and platelets through the passage is kept high enough to maintain the required tangential flow yet low enough so that damage to the red cells and platelets is minimized. Washing fluid can be added whereby dilution aids in removal of blood substances which can pass through the membrane. The washing fluid can be added during the entire time that the plasma and red cells flow through the passage thus leading to highly efficient processing.

The pump of the present invention provides pumping at a controllable rate with minimal damage to the blood cells and platelets and is useful in a number of blood processing applications. Anticoagulant fluid and/or other fluids, e.g., washing fluid, a diluent such as normal saline, a therapeutic agent, a diagnostic substance such as a contrast medium, etc., can be added in direct proportion to the amount of blood being pumped to fix the volumetric ratios of blood, anticoagulant fluid, washing fluid, etc. Or, the blood can be otherwise processed, for example, by hemodialysis, hemoconcentration, plasmapheresis, biochemical reactions, or other methods. Embodiments of the system can be used in blood removal and storage, intraoperative autotransfusion, or post surgical chest drainage with blood return.

BRIEF DESCRIPTION OF DRAWINGS

The invention will be better understood by reference to the figures of the drawings wherein like numbers denote like parts throughout and wherein:

FIGS. 8(d) and 8(e) are tables illustrating the wash or saline solution added to the blood mixture.

BEST MODE FOR CARRYING OUT INVENTION

Figure 1:
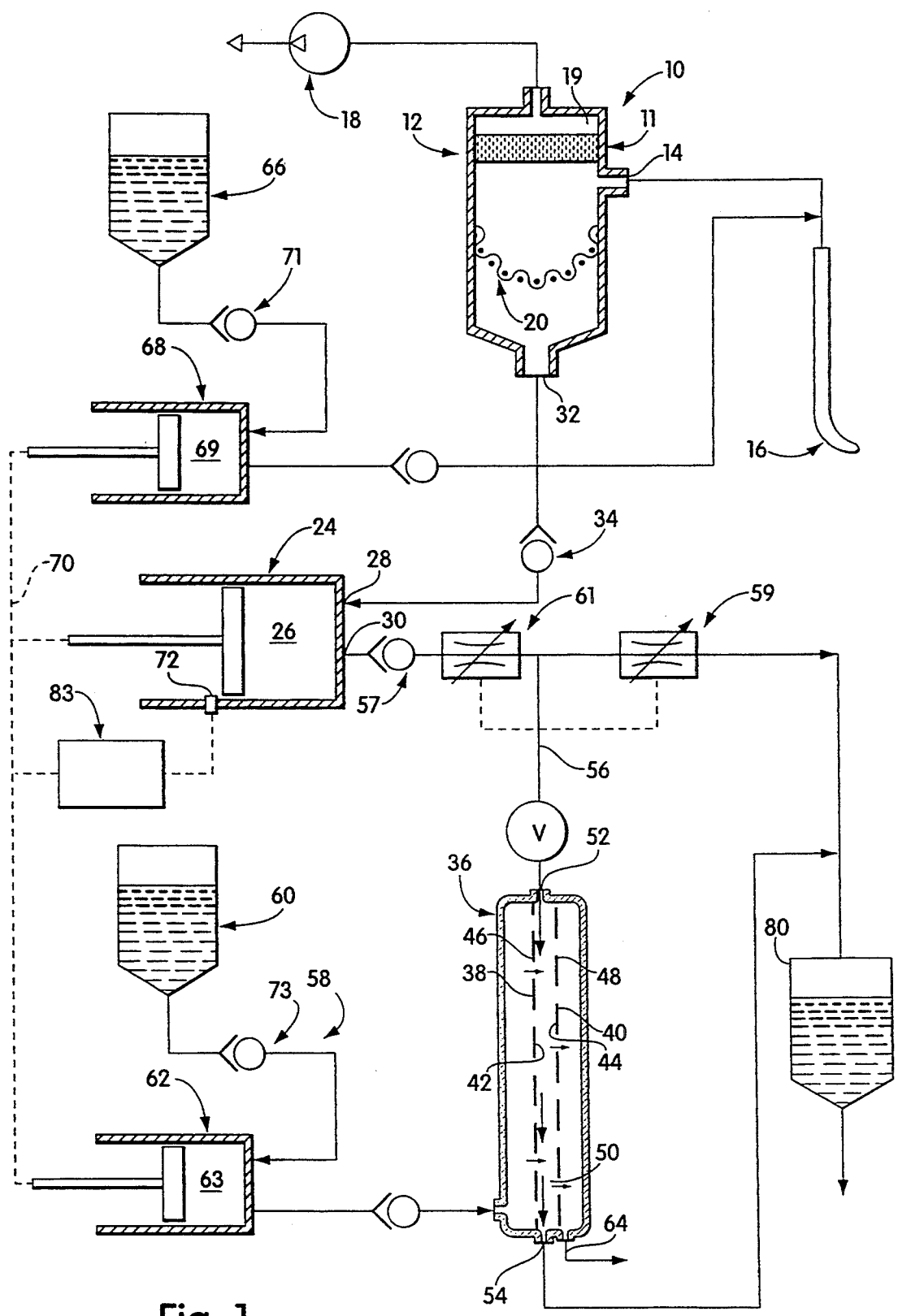
FIG. 1 illustrates, schematically, a method and apparatus in accordance with an embodiment of the present invention.

FIG. 1 illustrates, schematically, a blood filtering and tangential flow blood cell and platelet washing apparatus 10 in accordance with an embodiment of the present invention. The apparatus 10 includes a defoaming and coarse filtering unit 11 which includes a defoamer 12 having an inlet port 14 which serves for receiving a recovered mixture of healthy blood cells, platelets, fluid (including plasma), particulate matter and entrapped gases. The defoamer 12 is capable of removing at least a portion of the entrapped gases from the mixture to form a defoamed mixture. The term "entrapped gases" as used herein includes gases in bubbles and foam plus large slugs of air which may be picked up by a suction wand 16 when it is not drawing blood.

The recovered mixture of healthy blood cells, platelets, fluid, particulate matter and entrapped gases is generally picked up by the suction wand 16 through application of a vacuum from a vacuum source 18 to the defoamer 12 at a position above the inlet port 14. The vacuum source 18 communicates above the liquid level, namely with a non-liquid filled chamber 19, in the defoamer 12. Thus, the vacuum source 18 does not remove significant amounts of blood cells or fluid. The vacuum source 18 does remove at least a portion, generally most, of the entrapped gases.

A filter 20 which generally provides rough filtering to remove clots and other relatively large particles, in the embodiment illustrated a part of the unit 11, serves for removing at least a portion (the larger particle portion) of the particulate matter from the recovered mixture during and following the defoaming by the defoamer 12 to form a filtered mixture. It is also contemplated that the defoaming can follow the filtering or that the filtering can follow blood pumping. Indeed, two filters can be used, one before and one following blood pumping.

In accordance with the embodiment illustrated in FIG. 1 the filter 20 and the defoamer 12 are all part of the single defoaming and filtering unit 11 although separate units may be used instead. In operation the recovered mixture of healthy blood cells, platelets, fluid, particulate matter and entrapped gases enters the defoaming and filtering unit 11 via the inlet port 14 and the entrapped gases are pumped away from the chamber 19 by the vacuum source 18 while the healthy blood cells, platelets, fluid and particulate matter reach the filter 20. At least a portion of the particulate matter (particles larger than red blood cells) is held by the filter 20 while the healthy blood cells, platelets, and fluid, and generally a portion (the debris smaller than red blood cells and smaller than platelets) of the particulate matter, pass through the filter 20 for treatment as is described below.

A main pump 24 has a stroking or pumping chamber 26 having a pump inlet port 28. While FIG. 1 shows piston pumps and while such are usable in some embodiments of the invention, diaphragm pumps are preferred to minimize cell and platelet damage and to permit the diaphragm pumps to be part of an inexpensive disposable assembly. The pump inlet port 28 is arranged to receive the defoamed and filtered mixture. A pump outlet port 30 communicates with the pumping chamber 26 and serves as an outlet for the defoamed and filtered mixture. Between an outlet port 32 of the defoaming and filtering unit 11 and the pump inlet port 28, a valve 34, such as the float check valve shown, is located which serves as means for preventing flow from the pumping chamber 26 back towards the defoaming and filtering unit 11 and for allowing flow from the defoaming and filtering unit outlet port 32 to the pump inlet port 28 when the defoamed and filtered mixture is not being pumped out of the pump outlet port 30. In practice, the pumping chamber 26 fills with a batch of blood and other fluids picked up by the wand 16, that batch is pumped out of the pumping chamber 26, then another batch is collected in the pumping chamber 26, etc. Since bleeding rates vary greatly during an operation there are often times when the pump 24 is idle, i.e., receiving little or no blood and pumping only occasionally.

A tangential flow separator 36 forms an important part of one embodiment of the invention. The tangential flow separator 36 has first and second spaced apart membranes 38 and 40 having respective infacing surfaces 42 and 44 and respective outfacing surfaces 46 and 48. Both membranes are porous to aqueous liquids and the second membrane 40 will allow fluid and particulate matter smaller than red cells and than platelets (platelets are slightly smaller than red cells) to pass through it. Preferably the pores of the second membrane 40 will be too small to permit passage of red cells or platelets since if flow is interrupted some of the red cells and platelets can then pass through the pores leading to a loss of such cells and platelets. However, the pores can be large enough to allow red cells and platelets to pass through the second membrane 40 since during flow the cells and platelets are hydrodynamically prevented from passing through the pores. The infacing surfaces 42 and 44 define a narrow flow through passage 50 therebetween of no more than about 100 red cell diameters (no more than about 500 microns), preferably of no more than about 300 microns, across, the passage 50 extending from a separator inlet 52 to a separator outlet 54. A number of such passages 50 can be used in parallel or in series in the tangential flow separator 36. The passages 50 can be in a bundle of, for example, hollow fibers having porous membrane walls or can be a plurality of generally flat passages 50 made from membrane sheets.

Figure 2:
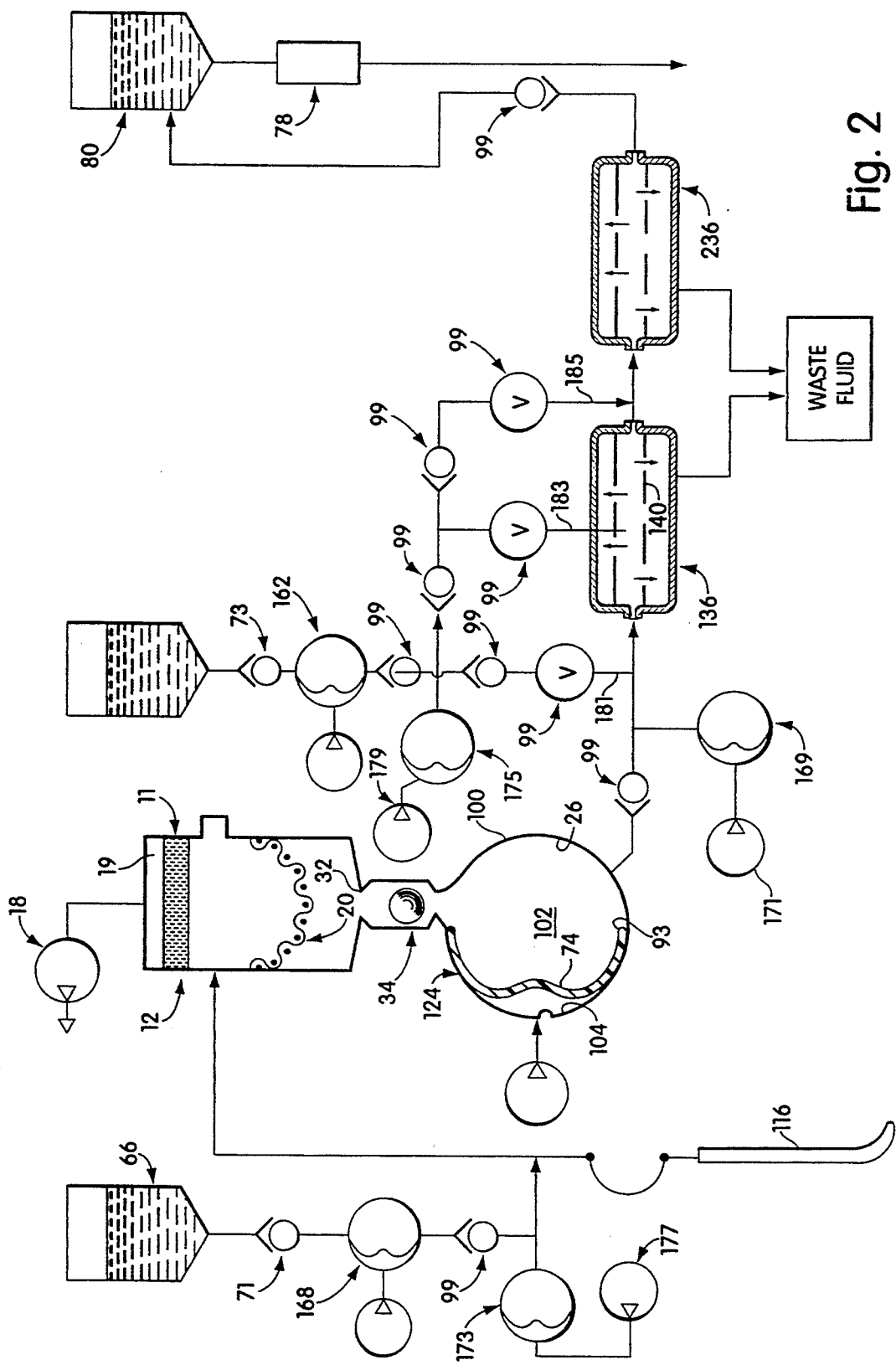
FIG. 2 illustrates, schematically, an embodiment of an apparatus in accordance with the present invention.
Figure 14:
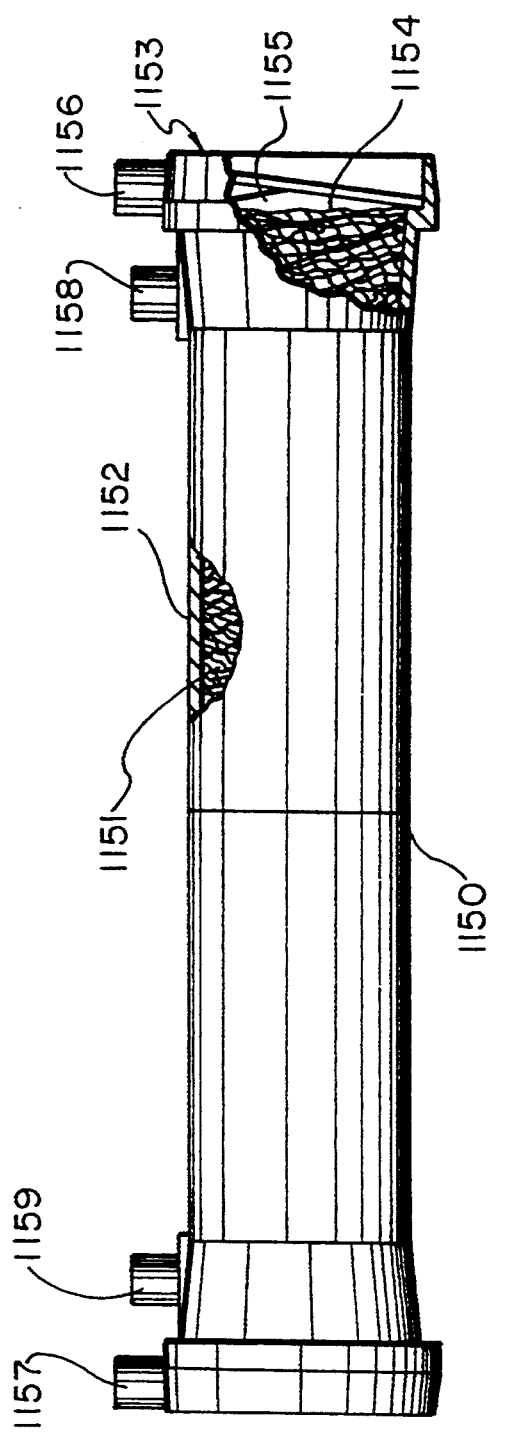
FIG. 14 is a diagram of a type of separator which may be used in the system of the present invention.

A plasma separator 1150 illustrated in FIG. 14 of the present invention is a type having a plurality of hollow fibers 1151 having porous membrane walls. Preferably a number of hollow fibers (which may number 4,500 individual hollow fibers) are each of approximately 0.7–0.83 meters square each in surface area and are housed in a tubular housing 1152 and are captured on either end by an end housing 1153 such that the ends of the fibers are captured in a manner (such as by a potting compound) so as to be open to the passage 1155. Passage 1155 has a tube 1156 as an outlet and a corresponding tube 1157 as an inlet. Tubes 1158 and 1159 are in communication with the interior of the housing 1152. In operation, blood is introduced into inlet tube 1157. As seen in reference to FIG. 2, and as described above, waste material will flow out of fibers, out through tubes 1158 and 1159 and to the waste bag while blood cells will travel through the fibers and out tube 1156 to the blood bag for reinfusion into the patient, or in the case of the separator being the first separator, into the second filter. Fibers usable in the separator are available from Mitsubishi Rayon as Polyethylene Microporous Hollow Fiber Membranes (EHF). The fibers are constrained and retained in a cylindrical jacket as shown as cylindrical jacket 136 in FIG. 10. Turning now to FIG. 2, blood from the main pump 102 enters and exits the device through inlets and outlets on either end of the jacket. Waste material which includes plasma and other material is removed from outlet port 202 and flows into the waste pump of FIG. 7 and then into waste fluid container 201 shown in FIG. 2.

The construction of the plasma separators 136 and 236 in the preferred embodiment is essentially identical in design and in materials to hemoconcentrators and plasma separators used in apheresis. However, unlike these separators, the separators of the present invention differ in (1) their intended use (2) the number of hollow fibers (3) the inside diameter and opening size of the fibers and (4) the length of the fibers. The fibers' inside diameter, their number and length are selected to give the surface area of fiber needed to remove the necessary amounts of waste fluid with low and atraumatic transmembrane pressure differentials and to achieve an excessively low pressure drop (under 100 mm Hg from the blood inlet port to the blood outlet port of each separator). In the hollow membranes of the preferred embodiment, the porous side of the membrane may be approximately 0.22 or substantially smaller than similar elements of comprising blood. Thus, only the blood fluids can be removed while red cells, white cells and platelets are retained within the hollow fiber lumen for removal and transit to the blood bag 80.

The filters may be a hydrophilic hollow-fiber cell separator, or may be of the hydrophobic variety. The difference between hydrophobic and hydrophilic fibers is that hydrophobic fibers generally require a prime unit of saline solution to "wet" the fibers while with hydrophilic fibers little or no such priming may be required. Such cell separators are available in many sizes and varieties and provide for specific blood separation applications.

Fluid from the pumping chamber 26 in FIG. 1 is delivered via a conduit 56 and past a valve 57 such as the check valve shown, which together serve as delivery means, to the passage 50, and more particularly to the separator inlet 52, generally at substantially the pumping pressure, P. A bypass valve 59 allows return of the defoamed and filtered blood to a blood storage bag 80 and subsequently to the patient without use of the tangential flow separator 36 or washing action. This can be used when the recovered blood is relatively clean and undamaged. Also, the bypass valve 59 can be automatically opened if blood flow rate from the main pump 24 exceeds the blood flow rate capability of the separator 36, for example, if bleeding during an operation is excessive for a time. This condition can be detected by a flow meter 61 and the valve 59 can be a solenoid valve actuated by the flow meter. The bypass valve 59 and associated tubing may also be used with other embodiments of the invention.

FIG. 1 also illustrates washing fluid delivering means 58 in accordance with an embodiment of the invention. A washing fluid supply 60 and a washing fluid pump 62, serve for delivering washing fluid at a pressure, $P_1$, against the outfacing surface of the first membrane 38, $P_1$ being sufficiently greater than P, whereby the washing fluid flows through the first membrane 38 and into the passage 50. The washing fluid is generally flowed in through the first membrane 38 along the length of the passage 50 to provide continuous and distributed diluting and washing action.

Fluid removing means, in the embodiment illustrated a conduit 64 from which waste fluid is removed, serves for removing a mixture of blood fluid, very small matter (smaller than red cells and platelets) and washing fluid from the outfacing surface 48 of the second membrane 40. A pressure, $P_2$, adjacent the outfacing surface 48 of the second membrane 40 is maintained at less than P. If desired a pump 65, of the nature illustrated in FIG. 7, may be included in the conduit 64 to further control the plasma flow rate and the pressure differential $P-P_2$.

The pressure differentials P-P and $P-P_2$ are maintained such that the washing fluid flows through the first membrane 38 and into the central narrow flow-through passage 50 at a desired rate. The membrane 38 generally uniformly distributes the washing fluid into the flowing blood over the entire length of the infacing surface 42 of the first membrane 38. Blood fluid along with washing fluid are likewise generally removed over the entire length of the infacing surface 44 of the second membrane 40 which defines the central narrow flow-through passage 50. Blood and washing fluid are thoroughly mixed within the passage 50 due to the relatively high blood velocity. The advantages of this method for washing fluid addition, compared to adding washing fluid before filtration, are considerable. First, the washing fluid continuously dilutes the blood when it is flowing through the passage 50 so that blood viscosity is reduced in all parts of the passage 50 and consequently fluid removal rates are higher. Second, sequential or serial dilution accompanying plasma removal results in decreased flow rate and consumption of washing fluid and more effective removal of unwanted constituents (e.g., particulate matter smaller than red cells and platelets, as well as anticoagulant).

The blood velocity through the passage 50 must be in a range such that a flow regime is realized in which a fluid boundary layer is hydrodynamically established immediately adjacent to the second membrane 40 which is such that blood cells and platelets are hydrodynamically prevented from layering upon and blocking the porous membrane Indeed, it is possible to use a porous second membrane 40 with pores large enough for blood cells and/or platelets to pass through with the blood cells and/or platelets being prevented hydrodynamically from doing so due to shear forces adjacent the membrane 40. Basically, the fluid velocity, V, must be maintained of the proper magnitude, as is known for plasmapheresis, to keep cells from either blocking or passing through the pores of the second membrane 40. The deposition of cells and platelets onto the second membrane 40 or the passage of cells and platelets therethrough is thereby hydrodynamically prevented in the manner known for plasmapheresis. This increases plasma flow through the membrane 40 and prevents or minimizes cell and platelet damage. The blood fluid velocity should not be too high or significant red cell and platelet damage can occur. Generally the velocity, V, of the blood through the passage 50 should be in the range from about 50 to about 1000 cm/min, more preferably from about 200 to about 500 cm/min. The broader range corresponds to shear rates from about 1000 to about 2500 $sec^{-1}$ based upon channels of from about 100 microns to about 250 microns across.

Figure 6:
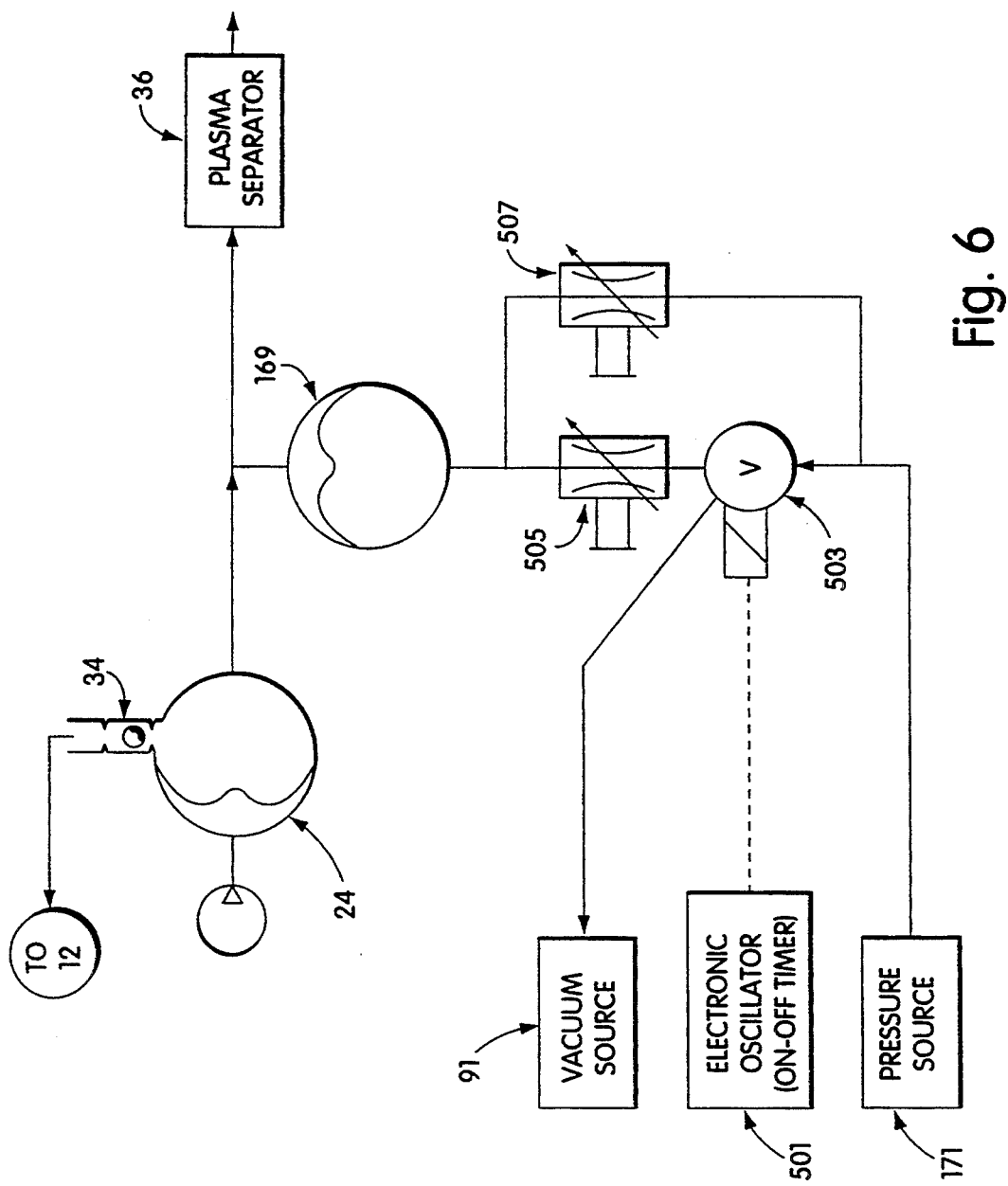
FIG. 6 illustrates, schematically, still another alternate embodiment of a portion of an apparatus in accordance with the present invention.

The complete mixing of red cells, white cells, and platelets with fluid within the separator blood flow-through passage 50 increases the rate at which fluid can be removed from the porous membrane 40 by decreasing the usual concentration of these cells near the membrane 40. Such mixing is achieved in part by high blood velocities. The use of oscillations in pressure or flow within the blood flow-through passage 50, which can be induced, for example, by providing oscillations adjacent the outfacing surface 48 of the membrane 40 (on the plasma side), provide additional mixing. Such oscillations can alternatively be superimposed on the actuating gas of the blood pump 24, the wash fluid pump 62, blood accumulator 169, wash fluid accumulator 175 or waste fluid accumulator (not shown). This may be accomplished by, for instance, use of a cycled solenoid valve 503 (FIG. 6) which provides a specific frequency and pressure, flow, or volume amplitude for optimal mixing. Flow control valves or orifices 505,507 are adjusted or selected for appropriate magnitude of oscillation. These oscillations may be used to change the pressure differential from blood to plasma sufficiently to periodically back flush the membrane 40. They may also be used to move the membrane 40 itself sufficiently to cause blood mixing.

The pressure, $P_2$, is generally near atmospheric pressure since conduit 64 usually simply leads to waste fluid storage (not shown). However, reduced pressure can be utilized or even pressures above atmospheric. All that is important is that $P_1$ be greater than P which in turn must be greater than $P_2$, Generally the pressure, P, will exceed the pressure $P_2$ by about 25 mm Hg to about 150 mm Hg, more preferably from about 50 mm Hg to about 100 mm Hg. Generally the pressure differential $P_1-P$ will fall within a range from about 1 mm Hg to about 50 mm Hg, more preferably from about 5 mm Hg to about 25 mm Hg. The relatively low pressure differential, P-P$_2$, can be utilized because of the fact that the cells and platelets are not held by and do not block the second membrane 40.

Figure 7:
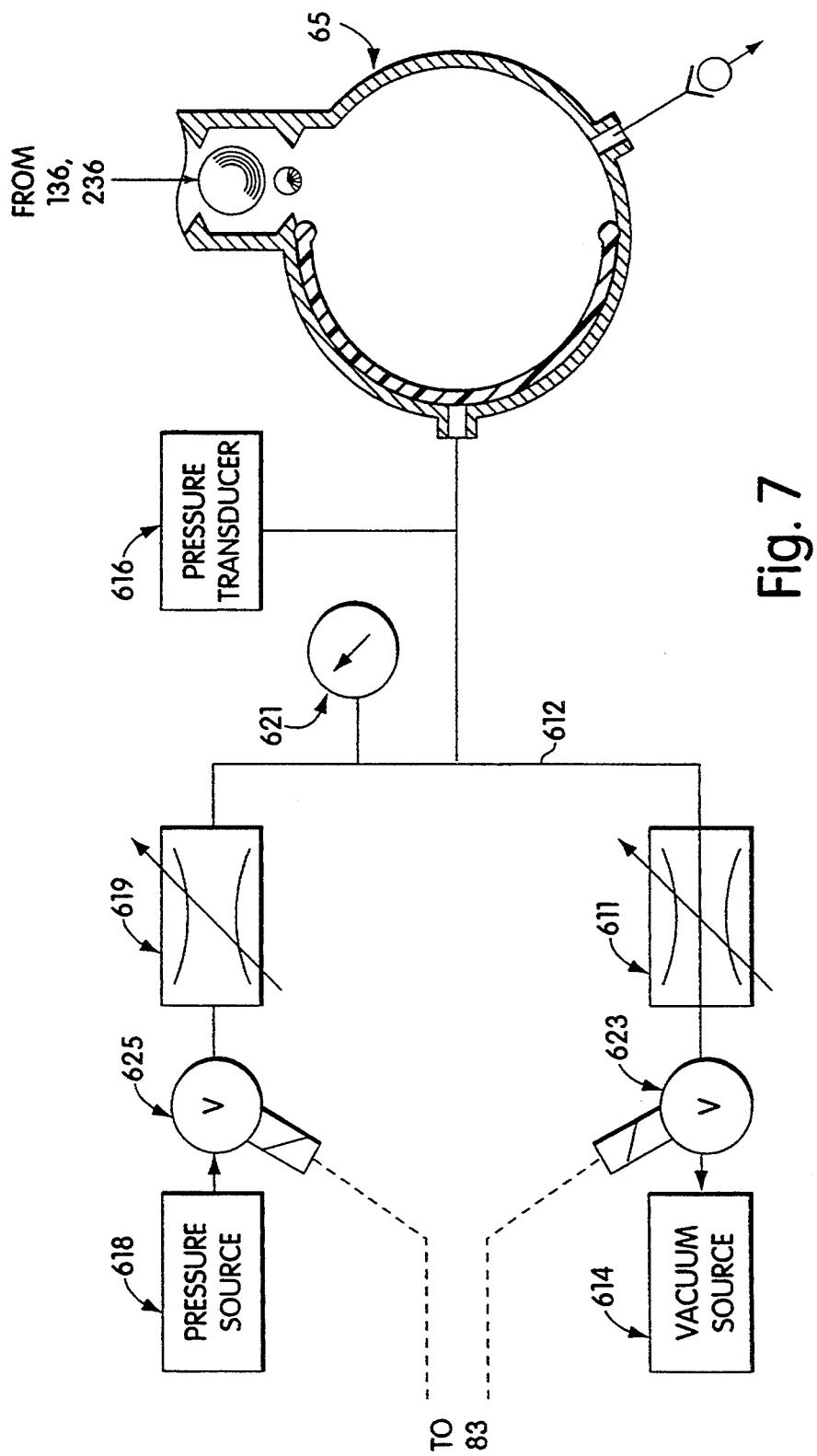
FIG. 7 illustrates, schematically, another alternate embodiment yet of a portion of an apparatus in accordance with the present invention.

As illustrated in FIG. 7, a waste fluid pump 65 may be used to control the rate of waste fluid removal and thereby the pressure, P$_2$, FIG. 7 illustrates a variation on the embodiment of FIG. 2 wherein the waste fluid pump 65 receives the outflow (controlled by the suction developed by the pump 65) of waste fluid from the separators 136 and 236 and delivers the waste fluid for disposal. However, the waste fluid pump 65 can be used with other embodiments of the invention, for example, when there is only a single separator 36. The waste fluid pump 65 can suitably be a diaphragm pump of the same nature as is the main pump 124 of FIGS. 2 and 3. However, the waste fluid pump 65 operates out of phase with the main pump 124 in that when the main pump 124 is pumping fluid the waste fluid pump 65 is filling with fluid and when the main pump 124 is filling with fluid the waste fluid pump 65 is pumping the waste fluid past an exit line check valve. The waste fluid pump 65 can operate at a fixed flow rate, if desired. Such can be accomplished by adding a flow meter 621, a pressure sensor 616, a pressure source 618, a vacuum source 614, appropriate orifices 611 and 619, solenoid valves 623 and 625 and a controller and timer 83 of the nature of that shown in FIG. 3 to control the vacuum in a conduit 612 leading to the pressurization side of the waste fluid pump 65.

Figure 8A:
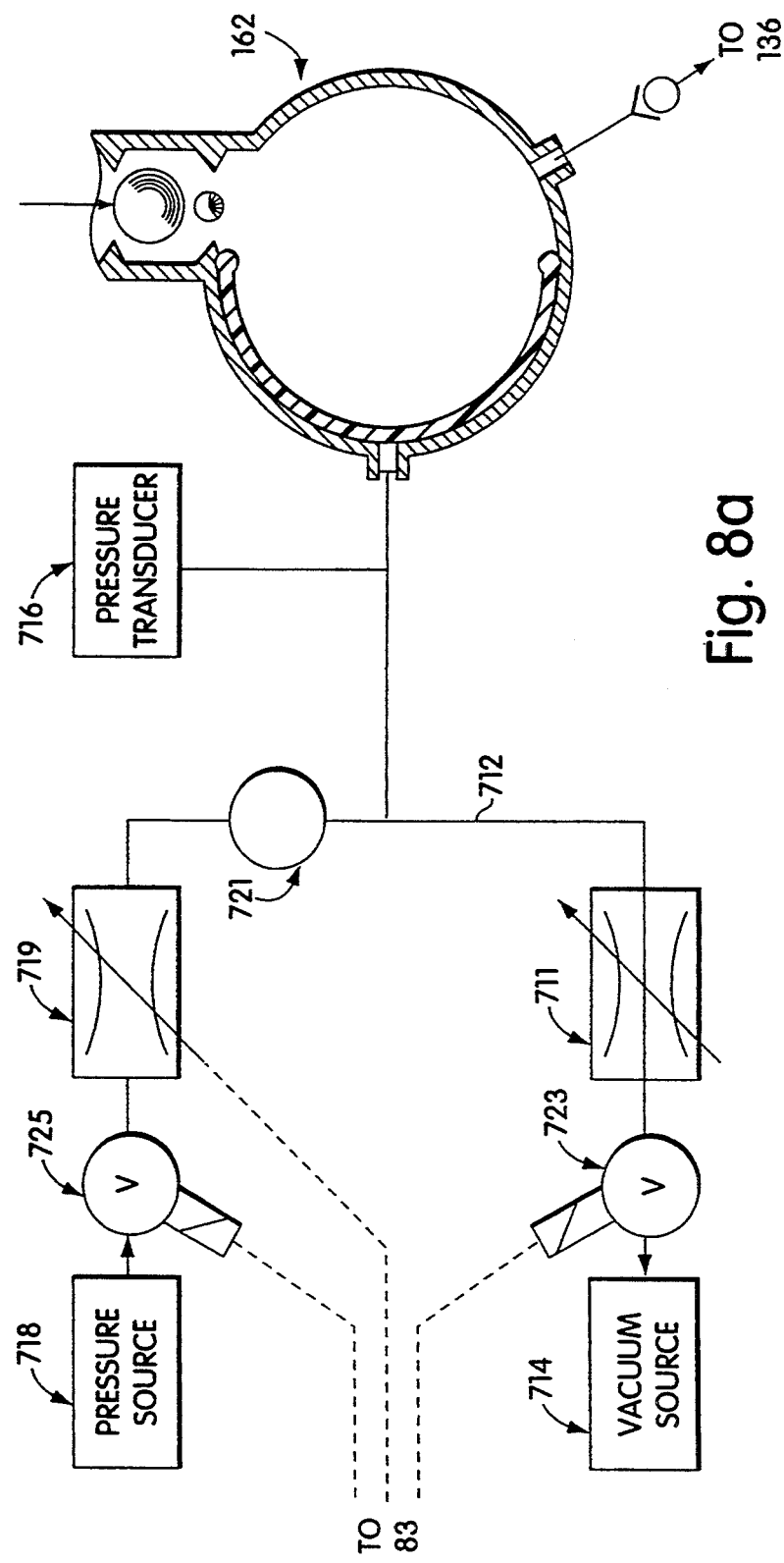
FIG. 8(a) illustrates, schematically, another alternate embodiment still of a portion of an apparatus in accordance with the present invention.

FIG. 8(a), which may be read in conjunction with FIG. 2, illustrates apparatus which can be used to control operation of the washing fluid pump 162. When the illustrated control scheme is used in conjunction with the apparatus shown in FIG. 7 for controlling operation of the waste fluid pump 65 the pumping volumes of the two pumps 162 and 65 can be coordinatedly selected to provide a given percent output hematocrit (usually in the range of 40%-60%) from the separators 136,236 when the input hematocrit to the main pump 124 is a selected value (for example, in the range of 5%-40%) which is less then the given percent. The necessary control of the washing fluid pump 162 can be accomplished by adding a flow meter 721, a pressure sensor 716, a pressure source 718, a vacuum source 714, appropriate orifices 711 and 719, solenoid valves 723 and 725 and the controller and timer 83 to control pressure in a conduit 712 leading to the pressurization side of the washing fluid pump 162. The controller and timer 83 can suitably control the size of the orifice 719. In one embodiment the volume pumped, per stroke, by the waste pump 65 can be a fixed volume and the volume pumped, per stroke, by the washing fluid pump 162 can be varied to provide a desired output hematocrit.

In accordance with one embodiment of the present invention anticoagulant delivery means are provided, in the embodiment illustrated in FIG. 1 an anticoagulant supply 66, from which anticoagulant is delivered in solution by an anticoagulant pump 68 to the recovered mixture of healthy blood cells, fluid, particulate matter and entrapped gases between the suction want 16 and the inlet port 14. The anticoagulant introduction means is desirable because the recovered mixture would likely form blood clots within the blood pumping and processing system without the addition of the anticoagulant. Furthermore, it is desirable that the anticoagulant be added early so as to prevent coagulation during passage through the wand connecting tubing and the filter 20.

In accordance with an embodiment of the present invention operation of the washing fluid pump 62 and of the anticoagulant pump 66 occurs along with pumping of the main pump 24 whereby each batch of blood pumped by the main pump 24 receives a proper amount of anticoagulant and of washing fluid. This is indicated, schematically, by the dashed line 70 in FIG. 1. In FIG. 1 a sensor 72 senses the "full" position of the piston of the main pump 24. Generally, stroking of the main pump 24 is initiated when the pumping chamber 26 is completely full. AT the same time, the pumping chambers, 69 of the anticoagulant pump 68 and 63 of the washing fluid pump 62, are completely full having been filled from the respective supplies 66 and 60 via appropriate valves 71 and 73. Stroking of pumps 62 and 68 generally occurs simultaneously with the stroking of the main pump While check valves are shown, other types of valves can be used with appropriate controls to open and close them.

It is desirable to have means for providing anticoagulant flow when the amount of blood being aspirated by the wound 16 is small. In such an instance the main pump 24 is not stroking very often and insufficient anticoagulant may be provided to the aspirated blood to prevent clotting in the coarse filtering unit 11. This can be accomplished by an electronic controller and timer 83 which has the capability to stroke the anticoagulant pump 68 independently of stroking of the main pump 24 and at a selected rate. Generally, independent stroking of the anticoagulant pump 68 will occur only when the main pump 24 has not stroked after a selected time. The electronic controller and timer 83 can advantageously be used to control and time pumping of the main pump 124, the wash fluid pump 62 and the waste fluid pump 63.

In accordance with a preferred embodiment of the present invention (as illustrated, for example, in FIGS. 2 and 3) the main pump 124 is in the nature of a diaphragm pump. This minimizes cell and platelet damage during pumping as compared to roller pumps and piston pumps. The diaphragm pump 124 includes a rigid housing 100 defining a biconcave chamber 102 which is divided by the diaphragm 74 into a stroking or blood pumping subchamber 26 and a pressurization subchamber 104. When the pumping subchamber 26 is full this fact is detected, for example, by a pressure measuring sensor 172 (see FIG. 3) which measures the pressure level in pressurization subchamber 104 as air is flowed in at a constant flow rate from pressurized gas source 204 (e.g., an air pump or cylinder). If the pressure increases above a threshold level in a selected interval of time, this indicates that the pumping subchamber 26 is full and pressurization is continued for a time period sufficient to pump all of the blood out of the pumping subchamber 26. If the pressure in pressurization subchamber 104 does not reach the threshold level, pressurization is discontinued at the end of the selected interval of time. After a time delay this procedure is repeated until threshold level is reached.

Note that the threshold level is not reached when the pumping subchamber 26 is not full since the pumping subchamber 26 is then in communication, via the open float valve 34, the float 35 of which is below its seat 37, with a partial vacuum. When the pumping subchamber 26 is full of liquid the float 35 floats upwardly against its seat 37 and is accordingly closed. With the valve 34 closed the pressure in the pressurization subchamber 104 rises to above the threshold value to the pressure, P, entering the plasma separator 36. Then a fluid, for example air, is pumped into the pressurization subchamber 104 for a time period sufficient to empty pumping subchamber 26. The diaphragm 74 is then forced rightwardly in FIG. 2 until it generally matches the shape of the wall of the biconcave chamber 102. At that time stroking of the main pump 124 is complete.

At the end of the pumping time period the defoamed and filtered mixture from the defoaming and filtering unit 11 can again flow past the ball check valve 34 and begin refilling the pumping chamber 26. The float 35 of the float valve 34 generally has a specific gravity of 0.8 to 1.0. This assures that when the pumping subchamber 26 is full the float 35 will float on top of the fluid and the float valve 34 will be closed. It also assures that any air and foam will not be dense enough to close the float valve 34 whereby the air and foam will be expelled upwards from and out of the pumping subchamber 26.

As has previously been stated the operation of main pump 124 can serve to trigger operation of the washing fluid pump 162 and of the anticoagulant pump 168 for the same pumping time period (for one ejection stroke). Thus, when the pressure is introduced into the pressurization subchamber 104 of the main pump 124, a like action takes place in similar diaphragm pumps 162 and 168. Control of activation of the various pumps 124,162 and 168 can be via use of a conventional electronic controller/timer 83 which, on receiving a proper signal from the sensor 172, as indicated schematically by dashed line 85, open the solenoid valve 87 while keeping the solenoid valve 89 closed. The solenoid valve 87 connects to a gas pressure source 204 while the solenoid valve 89 connects to a vacuum source 91. With the valve 87 closed the valve 89 can be opened to evacuate the pressurization subchamber 104 and draw the diaphragm 74 leftwardly in FIGS. 2 and 3. The various valves 99 illustrated are triggered or automatically opened check valves, which open in proper sequence with the pumps. Such valves may be float valves, mechanical check valves, solenoid valves, or electromechanical tubing pinch valves.

Flow control means 202, such as a flow control valve or fixed orifice, can advantageously be included to adjust or control the air flow rate into the pressurization chamber 104. This assures that the pressure sensed by the pressure sensor 172 is determined by the pressure in the pressurization subchamber 104 rather than by the pressure of the gas pressure source 104. The flow control means 202 also partially controls the rate of flow of blood out of the pumping subchamber 26.

Figure 3:
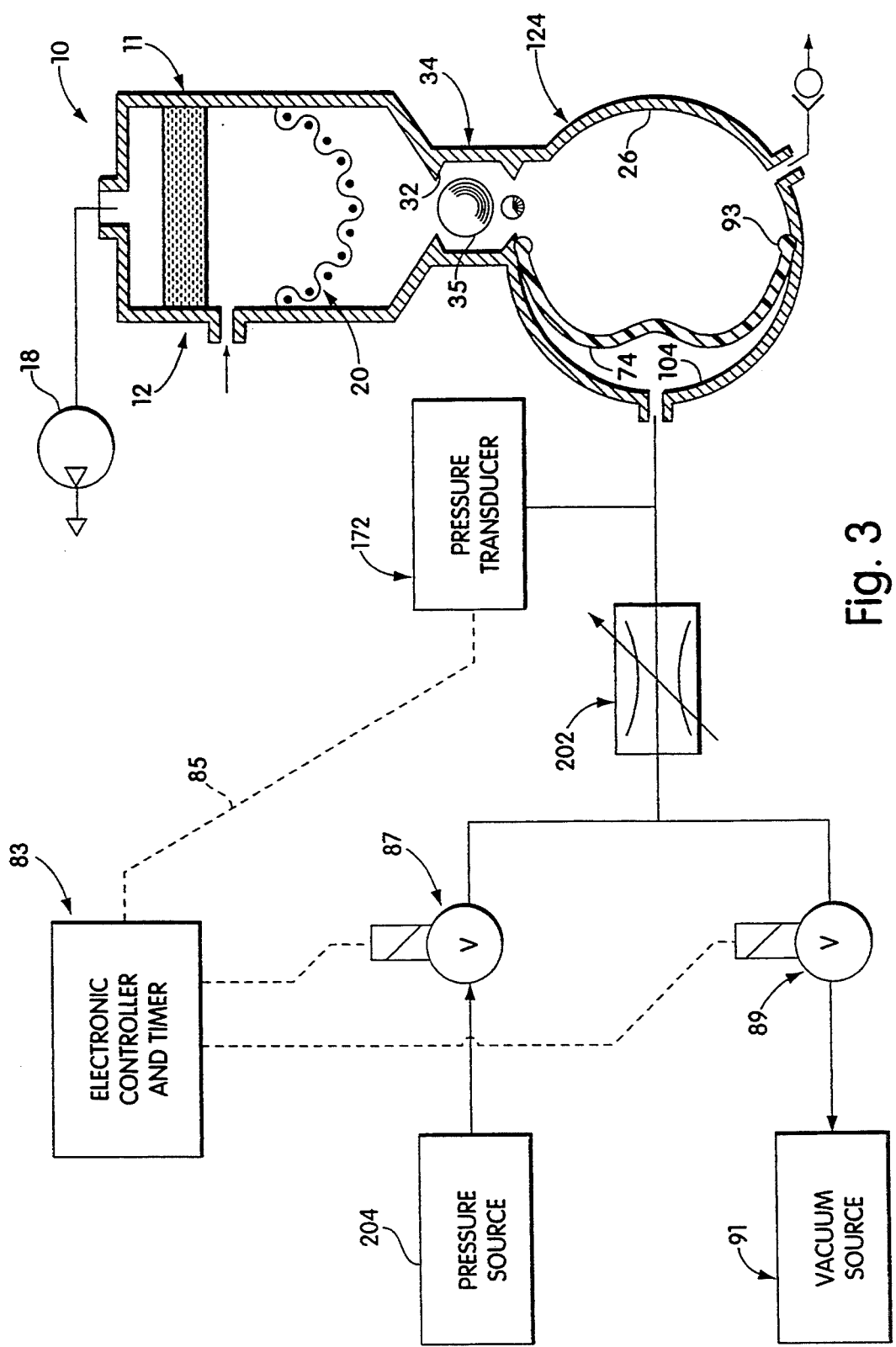
FIG. 3 illustrates, schematically, an embodiment of a portion of an apparatus in accordance with the present invention.

Referring to FIGS. 3 and 7, the electronic controller and timer 83 can provide electronic timing functions which turn the solenoid valves 87, 89 and 623 and 625 ON and OFF. When the main pump 124 (of FIG. 3) is full of blood, the electronic controller and timer 83 can turn the solenoid valve 87 on and apply air pressure to the main pump 124. This begins election of blood. The source air pressure can be made relatively high (5 to 15 psig) and the flow controlling orifice 202 relatively small so that the pressure drop due to air flow across the orifice 202 is appreciably larger than the pressure drop due to blood flow through the main pump outflow check valve, blood flow through the separators 136, 236 and the blood bag height.

The total blood flow pressure drop typically ranges from about 0.5 psi to 3 psi, depending on the viscosity of the blood which varies with blood hematocrit. Inlet blood hematocrit is nominally anywhere within the range of 5–40% (volume percent of red cells in total fluid picked up). With the air flow pressure drop predominating, the time for ejection of all blood from the main pump 24 varies little with blood hematocrit, which is the objective. This time is main pump (stroke) volume divided by air flow rate. The change in blood volume is equal to the change in air volume. The electronic termination of ejection (pumping) time period and initiation of the blood filling time period is set slightly longer in time than that calculated to provide emptying in order to ensure complete ejection by main pump 24. The desired condition of constant flow through the plasma separators 136,236 is approximated by having a long ejection time and a short fill time. For example, the actual ejection time may be about 16 seconds with a timed ejection of 17 seconds and a fill time of 3 seconds for a total cycle time of 20 seconds. Then, actual ejection is 80% of the total (cycle) time, or about as close to 100% as is feasible with this scheme of operation, and close enough for efficient use of the plasma separators 136,236. The electronic controller and timer 83 sets the fill time sufficiently long (slightly longer than the actual time to fill) to ensure that complete filling will always occur. Actual fill time is controlled by the fill vacuum level and the fill needle valve or orifice.

The main pump 124 senses filling by initiating pressurization for ejection. The electronic controller and timer 83 looks at the rise in pressure in the air drive line to the main pump 124. This air pressure is virtually identical to the blood pressure because the flexible diaphragm 74 (when not supported by its housing when the main pump 124 is full or empty) has no pressure drop across it. If the main pump 124 is not full of blood, the float valve 34 will not close and the pressure will not rise above the reservoir vacuum level when measured a selected time, e.g., one second, after ejection pressurization begins. When ejection pressurization is terminated, a time delay of, e.g., two seconds, for filling occurs, and ejection pressurization begins again. When the main pump 124 is full of blood, the initiation of ejection closes the float valve and the air actuation pressure rises above an "ejection threshold" pressure (about +10 mmHg). The electronic controller and timer 83 does not terminate ejection when this "threshold" pressure is exceeded but continues it for a timed interval (i.e., a total of 17 seconds).

The actuation air pressure rises when main pump ejection is complete and the diaphragm is against the rigid pump housing. A "maximum pressure threshold" is set (perhaps 4 psi) at which ejection is immediately terminated and filling begins. However, a new ejection cycle will not begin until the complete cycle time (i.e., 20 seconds) has elapsed.

This maximum pressure termination of ejection prevents the main pump 124 from being exposed to high pressures and indicates to the actuator logic that complete blood ejection has occurred. If the timed end of ejection occurs without a maximum pressure threshold signal or termination, then it indicates that complete ejection has not occurred and a warning (of improper operation) may be provided to the user. It is advantageous to actuate the blood pump so that it always fills and empties completely.

The wash pump 62 is operated the same as the main pump 124 except that ejection of the wash pump 62 only continues when main pump 124 ejection continues, that is when the main pump 124 is full. Both pumps initiate ejection at the same time, test to see if the respective pump is full at the same time, and begin filling at the same time. Wash pump flow is variable as is described below. The wash pump 62 always fills completely, but does not empty completely.

The waste pump 65 is actuated at the same time as the main pump 124 but its filling duration is the main pump 124 ejection duration, and its ejection is the main pump 124 filling period. It has no test pulse to determine whether it is full or not. It is always operated to empty completely, but does not fill completely.

The basic control concept is to maintain the main pump 124 at an average flow rate, to maintain the waste pump 65 at an average flow rate and to vary the wash fluid pump 62 to achieve a flow rate which depends upon inlet blood hematocrit (which, as described herein, is a function of the difference in pressure across the first separator) and which results in an outlet hematocrit of 35%–65% (nominally 50%).

If, for example, the main pump 124 flow rate is an average value of 250 ml/min., the waste pump 65 flow rate is selected to give a 40% output hematocrit at a 5% inlet hematocrit with no wash fluid addition. This amounts to removing 92% of the plasma initially present without adding any wash fluid. Even a large error in wash fluid flow can be tolerated with the outlet blood hematocrit remaining in the desired 35% to 65% range.

Operating in the manner just described provides substantially constant outlet blood hematocrit (for example, in the range of 40%–60%) independent of the inlet hematocrit (for example, over the range of 5% to 40%) and source of blood (rapid bleeding and relatively undamaged; mixed with bone fragments and fat; or highly hemolyzed); addition of wash fluid to achieve plasma removal efficiencies of 90% or above; minimal surface area of the plasma separators 136,236; and maintenance of high blood quality (low hemolysis caused by pumps and separators; high platelet recovery).

The manner in which the outlet blood hematocrit is maintained at the desired level of 35% to 65% is accomplished by measuring the pressure drop across the first separator 136 shown in FIG. 2. It is known to those skilled in the art that a pressure differential between two points across a plasma separator, such as that shown in FIG. 2 is indicative of the level of hematocrit of blood. This pressure drop is dependent upon inlet blood viscosity which is directly related to hematocrit. Viscosity also depends on blood temperature. Thus if the pressure drop from one point (prior to the entrance of the blood into the first separator 136 of FIG. 2) is determined and the pressure of the blood after passage through the first separator can be measured (provided blood flow rate remains constant) the hematocrit level of the blood entering the first filter 136 can be determined. To accomplish this, a first pressure is measured as the blood pump actuation pressure from which is subtracted the pressure which is measured through use of a suitable pressure transducer positioned immediately following the first separator 136 shown in FIG. 2. The pressure drop is proportional to and correlates accurately with the blood hematocrit. This pressure drop is monitored continuously by the microprocessor controlling the apparatus of the present invention. Thus, when a high inlet hematocrit level corresponding to a high pressure drop across the separator is detected, the greater the volume of saline solution which will be delivered by the saline pump at the point following the first membrane separator 136. When a smaller pressure drop is detected, indicating a lower inlet hematocrit level, the lesser the volume of saline which is delivered to the filtered blood exiting from the first separator. Thus, by measuring the pressure differential of the blood pump and the pressure at the outlet of the first membrane separator, the pressure drop and thus hematocrit can be determined so that the appropriate amount of saline may be delivered depending upon the inlet hematocrit of the blood entering into the first filter 136. Alternatively, the hematocrit level may be determined without measuring the pressure drop across two points as described above. This may be accomplished by measuring the pressure and the microprocessor controlling the apparatus of the present invention invoking a look-up table of pressure/temperature values to directly determine the hematocrit level. Thus, in a simple manner involving only the detection of and subtraction of pressure levels at two known points, as well as blood temperature, the desired outlet hematocrit level of the blood can be carefully controlled in a continuous manner. Of course, it will be understood that the present invention may be modified so as to allow for variable (but still controlled) outlet hematocrit levels as desired by the user of the system.

As mentioned earlier, in the ejection of saline solution from the saline pump into the first separator, the amount of saline may be varied for each blood pump stroke and saline pump stroke because the inlet hematocrit level of the blood may change from one pump stroke to another. The desire is to maintain the outlet blood hematocrit processed to the blood bag 80 to be in a range of 40% to 60%. The blood inlet hematocrit is determined by not only the pressure drop across the first plasma separator but by the blood inlet temperature as well, since inlet blood viscosity is a function of both the hematocrit and temperature of the blood. Correction of the pressure drop measurement for temperature is necessary for maximum accuracy and the closest correlation of pressure drop to hematocrit. This is due to the fact that the temperature of the blood determines its viscosity and must be accounted for in any calculation to accurately measure the pressure drop across the first plasma separator. The pressure drop is in direct proportion to viscosity as given by the following equation:

$$\Delta P = C_1 \mu$$

where $\mu$ is the blood viscosity In the preferred embodiment for purposes of correlating temperature to viscosity, we have defined a temperature $T_0 = 24°$.

The data for the correlation of hematocrit with pressure drop is taken at 24° C. Then, $$\Delta P_0 = C_1 \mu_0 = 32 \, C_2(H_1),$$

where $H_1$ is the inlet blood hematocrit and $C_1$ and $C_2$ are constants. At any other blood temperature $T_1$, the pressure drop is $$\Delta P_0 = C_1 \mu_1$$

Then, to correlate this pressure drop with the hematocrit and $\Delta P_0$, $$\Delta P_0 = \frac{\Delta P_1}{\mu_1} \mu_0 = \Delta P_1 \frac{\mu_0}{\mu_1}$$

The data of FIG. 1 relates viscosity with temperature at four hematocrits. A correlation of this data was made assuming $$\frac{\mu - \mu_0}{\mu_0} = C_2 (T - T_0)$$

Then, $$\frac{\mu}{\mu_0} = 1 - C_2 [T - T_0]$$

With $C_2=0.01804$, the maximum error for this analytical prediction is 4% at $T=40°$ C. Then the complete analytical expression is:

$$\Delta P_0 = \frac{\Delta P_1}{1 - .01804 [T - 24]}$$

where

T=Inlet blood temperature, °C.
$\Delta P_1$=DP, the measured pressure drop
$\Delta P_0$=A value which correlates with blood hematocrit at $T_0=24°$ C. and is used in a software look-up table (described below) to set the saline pump rate.

Figure 8B:
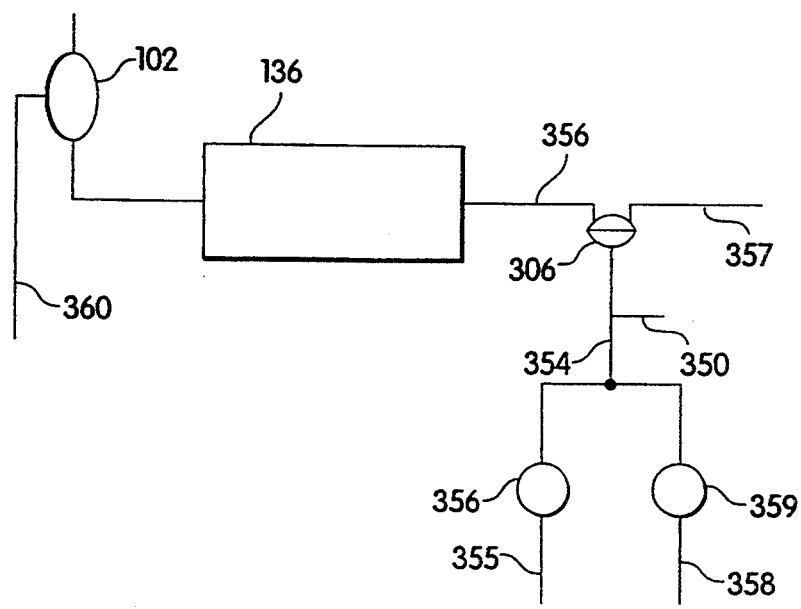
FIG. 8(b) illustrates, schematically, the apparatus of the present invention for the sensing of the pressure drop over the first separator.

FIG. 8(b) illustrates a variation in detail of the embodiment of FIG. 2. In FIG. 8(b), the blood pump 102 from FIG. 2 is illustrated. In addition, separator 136 corresponds to the first separator of FIG. 2. The pressure drop, if any, after the first separator 136 is measured at the pneumatic actuation line 354 for pneumatic valve 306 with its diaphragm in mid-position. A pressure transducer 350 measures this pressure during blood pump ejection.

Figure 8C:
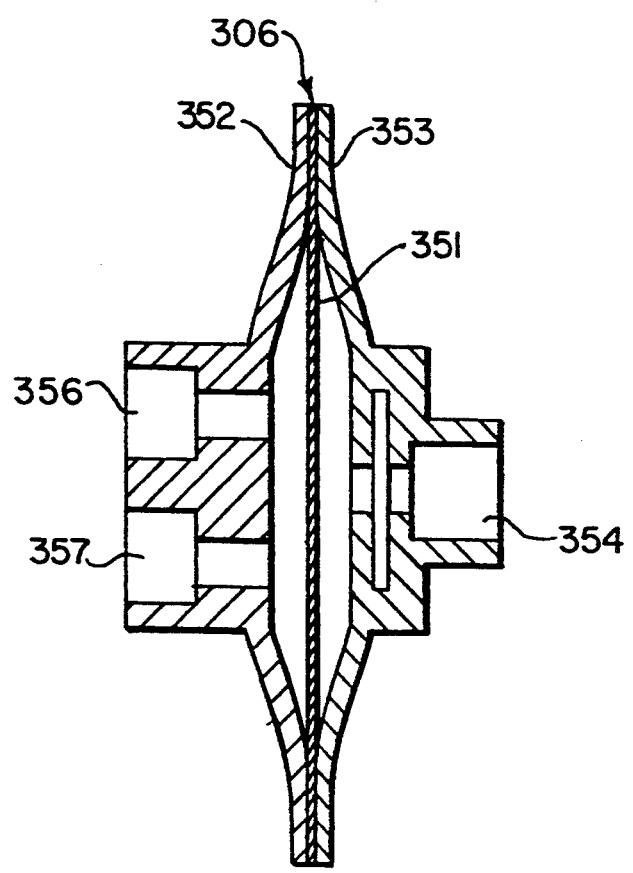
FIG. 8(c) illustrates a form of a pneumatic valve used in the present invention.

FIG. 8(c) illustrates a pneumatic valve which may be used with the present invention and in particular as pneumatic valve 306 in the embodiment of FIG. 8(b). Valve 306 is composed of two generally opposed and matching concave shells 352 and 353, like diaphragm pump housing 102, with a relatively flexible diaphragm member 351 interposed between the concave shells 352 and 353. One shell has attached to it thru tube members 356 and 357, the function of which will be explained below. The opposite shell has attached to it a thru tube member 354. The diaphragm member 351 is placed in its mid-stroke midway between the two supporting walls 352 and 353 to ensure that the diaphragm is unsupported to allow for pressure readings to be taken. It will be understood that the the tube 354 may be attached, as shown in FIG. 8(b), to a source of pressure or vacuum. Pneumatic line 354 is in communication with a valve 356 which may be a solenoid valve or other suitable valve. The valve 356 is in turn connected to a source of vacuum 355. The line 354 is also in communication with a solenoid valve 359 which is in turn connected with a source of pressurized fluid 358, preferably air or other gas. The operation of the pneumatic valve may be seen to be similar to that shown and described above with respect to the operation of the blood pump control illustrated in FIG. 4. In operation, the diaphragm may be moved from a position midway between the walls, as illustrated in FIG. 8(c), to a position (not shown) in which it occludes the openings of tubes 356 and 357 by the opening of solenoid valve 359 and the entry of pressurized fluid into line 354. This pressurized fluid will enter the space formed between the diaphragm 351 and wall 353 and will cause the diaphragm to move (to the left in FIG. 8(c)) so as to decrease the space between the diaphragm 351 and wall 352. It will be appreciated that when the diaphragm moves all the way to the left in FIG. 8(c), openings 356 and 357 will be occluded. This has the effect of causing an interruption of any flow through the valve. When it is desired to allow flow through the valve, the source of vacuum 355 will be activated through solenoid valve 356. The vacuum will move the diaphragm away from its contact with the openings in tubes 356 and 357 and will allow flow through the valve.

When the diaphragm is placed in its midpoint position illustrated in FIG. 8(c), it may be used in combination with pressure transducer 350 to measure the pressure in the fluid passing through the valve 306 during blood pump ejection. The midpoint position for the diaphragm is to ensure that the diaphragm is unsupported and will provide a negligible pressure drop between blood in the pneumatic valve and actuation air on the other side of the diaphragm. The pressure of the blood contained in the blood pump is determined by a pressure transducer 360 shown in FIG. 8(b). The pressure differential sensed by the pressure transducers 350 and 360 during blood pump ejection will give an indication of the pressure drop after the blood has passed through the first tangential filter and thus, as described in this disclosure, an indication of the hematocrit level of the blood.

Figure 9:
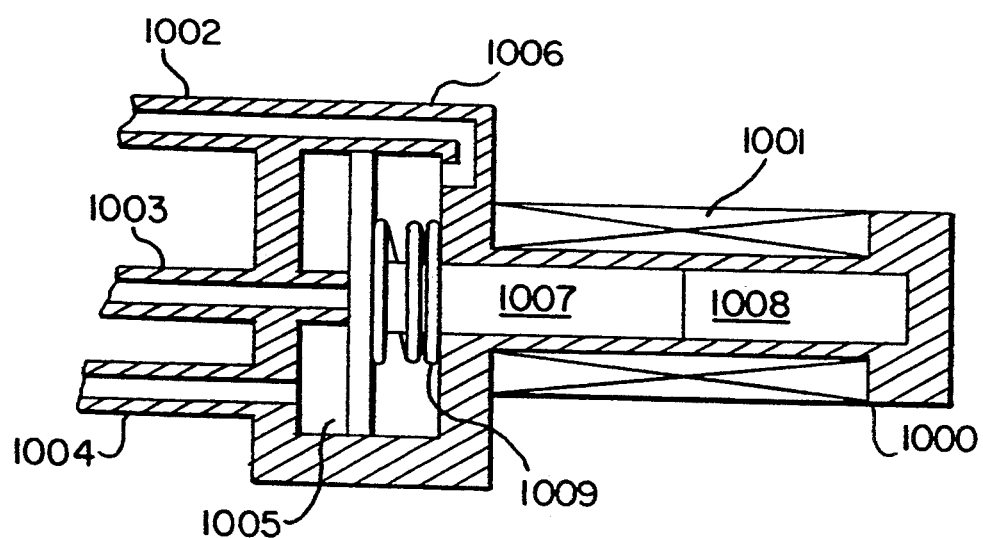
FIG. 9 is an illustration of a pulse width modulated valve.

As discussed above, once the hematocrit level has been determined, the saline or wash fluid pump, shown in one from in FIG. 8, will be selectively controlled to inject a predetermined amount of wash fluid into the line 357 exiting the first filter of FIG. 8(b). Injection is controlled by the amount by which the diaphragm in the pump body, such as the diaphragm 713 shown in FIG. 2 moves within the housing 162. It will be appreciated that the amount of movement of the diaphragm 713 depends on the amount of pressure introduced into the pump body. The flow rate of fluid introduced into the pump through a pressure source such as source 718 in FIG. 8 may be controlled through a plurality of switches (S1 through S5 in FIG. (8d)) which allow or prevent a predetermined amount of fluid from entering a conduit leading from a source of pressure and into the pump housing 713. These switches may be in the form of multiple solenoid switches or a single switch with a variable output. For example, in the preferred embodiment, five switches may be utilized which have a variable flow rate output. Various combinations of these five switches will control the amount of air being introduced into the pump body, thus controlling the quantity of saline ejected out of the pump and into the line leading from the first membrane filter. The flow rates of the five switches may be as follows: the first solenoid valve may have a flow of $\times$, the second of $2\times$, the third of $4\times$, the fourth of $8\times$ and the fifth of $16\times$. In operation, a combination of the valves open and closed gives a total sum range from 0 (opening none of the switches) to $31\times$ (the total of opening all the switches to air flow). The selection of combinations giving these flow rates is given in FIG. 8(d). In order to control which, if any, of the switches will be opened or closed in the scheme of FIG. 8(d), the pressure drop measured across the first filter will cause the software operating the system (to be described in detail below) to address a look-up table shown in FIG. 8(e) of the drawings. For example, if the drop in pressure across the membrane is 99 mm, the look-up table will indicate that this situation corresponds to Entry 15. Entry 15 in the table of FIG. 8(d) indicates that switches 1, 2, 3, and 4 are opened to air flow, thus causing the diaphragm to move a predetermined amount within the housing, and thus pumping a predetermined amount of wash fluid into the line leading from the first membrane filter. Since, as mentioned earlier, the wash pump always is filled with fluid prior to ejection, by the above technique, a predetermined amount of fluid may be ejected since in each instance the total amount of fluid in the pump chamber before pumping will be known. Of course, other schemes may be used to control the amount of fluid ejected from the pump housing. FIG. 9 illustrates yet another embodiment which may be used in place of the multiple solenoid switches. In FIG. 9 is shown a pulse width modulated valve (PWM) 1000. This commercially available valve is a single valve which has a variable output and is controlled in the same way as the multiple solenoid valves shown in FIGS. 8(*b*) to achieve the desired air flow rate out of the valve at each measured value of the difference in P. The pulse width or open period of the PWM valve is controlled electrically with a fixed frequency of operation. The pulse width or duration is a function of the measured difference in P. The relationship of pulse width and the difference in P is established by an equation or look-up table developed on a similar basis to the tables (FIGS. 8(*d*) and (*e*)) developed for the multiple valve embodiment. Pulse width valve directly controls air flow rate to the saline pump which indirectly controls the saline flow during saline pump ejection, as described above with respect to the multiple valve embodiment. PWM 1000 has an outer elongated housing 1001 with a number of tubes 1002, 1003 and 1004 carried at one end of the housing 1000. The tubes are open to the outside of the housing 1001 as well as open into a chamber 1005 within the housing. Within the chamber is disposed a seal disk 1006. The seal disk has fixed to its center an elongated armature 1007 which is contained in a tube or core 1008. A spring 1009 biases the disk and attached armature to the left in FIG. 9 and against the tube openings 1003 and 1004. Tube 1004 provides an inlet for air flow into the chamber 1005 of the tube 1003. In this position there will be no air flow through tube 1004 into the chamber 1005 and out tube outlet 1003. Surrounding armature 1007 is a core 1008 which upon application of an electrical current therethrough in a manner known in solenoids will cause the armature to move to the right as seen in FIG. 9, thus opening the passage to allow air to pass from tube 1004 through to and out tube 1003. Tube 1002 acts to exhaust air being displaced by movement of the disk 1005. Alternatively, if the armature were to be moved back and forth, left to right in FIG. 9, it can be seen that the number of such movements will allow a predetermined amount of air to be moved out the tube 1003. This allows precise delivery of air to the various pumps in the present invention, to allow, in the case of the wash pump, precise delivery of air and subsequent delivery of wash fluid. Just as the multiple solenoids or the pulse width modulated valve may be used to control the operation of the wash fluid pump, such solenoid valves or single pulse valve may be utilized to control the operation of the blood pump and the waste pump illustrated in FIG. 2, the operating sequence of which is described above.

Figure 10:
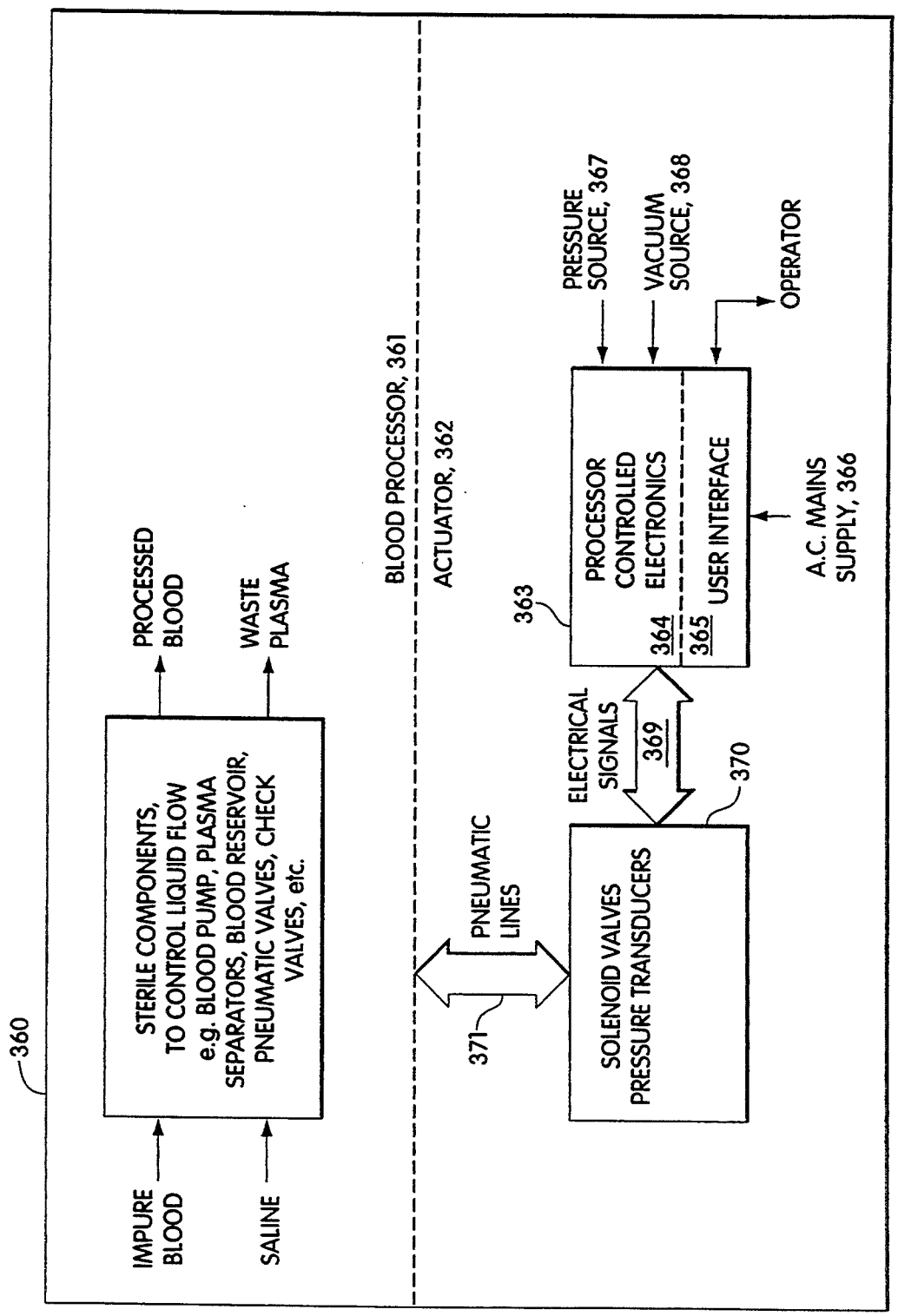
FIG. 10 is a schematic diagram of the overall system of the present invention.

FIG. 10 is a block figure which illustrates the overall building blocks of the system of the present invention. As seen in FIG. 10, the system 360 can be considered as being in two major subsystems, a permanent subsystem 362 and a replaceable, disposable subsystem 361. The disposable subsystem contains the elements generally shown in FIGS. 1 and 2, comprising the pumps, blood containers, the filters, lines for transporting blood, saline wash solution and waste fluid, pneumatic valves, pressure transducers, and pneumatic (pressure and vacuum) lines for actuating the various pumps and pneumatic valves disclosed. The disposable subsystem may be selectively detachable from the permanent subsystem 362 so that it can be replaced for use of the system by another patient. The only points of contact between the permanent and disposable subsystems will be the pneumatic lines which are selectively connectable and detachable from each other. The pneumatic connections will perform and control all operations with the components in the disposable system. It will be appreciated that this arrangement assures that blood from a patient which might be contaminated will not in any way come in contact with the permanent subsystem or the following patient's system since a new disposable system is utilized with each new patient. The pneumatic connector may be of any suitable type known to those of skill in the art and will include a interconnecting fitting to connect the pneumatic lines in the disposable subsystem to the pneumatic lines 371 in the permanent subsystem. As illustrated in FIG. 10, the permanent subsystem includes an electrical control portion 363 which has a user interface 365 which may be suitable switches, keyboards or other controls to allow the user to operate the device of the present invention and to monitor its functions. The electrical control portion is powered by an A.C. main power source 366, but as desired a D.C. or portable source of power may be used. The interface unit sends instructions to an electronics section 364 which may contain a microprocessor, memory devices and other electronic components to control a source of pressure 367 and of vacuum 368 through suitable electrical control lines 369 to the solenoid valves to control operation of the pumps and pneumatic valves described above. In addition, the pressure measured by the various pressure transducers described above will be sensed and carried through pneumatic lines 371 to the electrical control portion to be used to, for example as described above, measure the hematocrit in the blood after the first filter and control the amount of saline wash fluid introduced into the system.

Figure 11A:
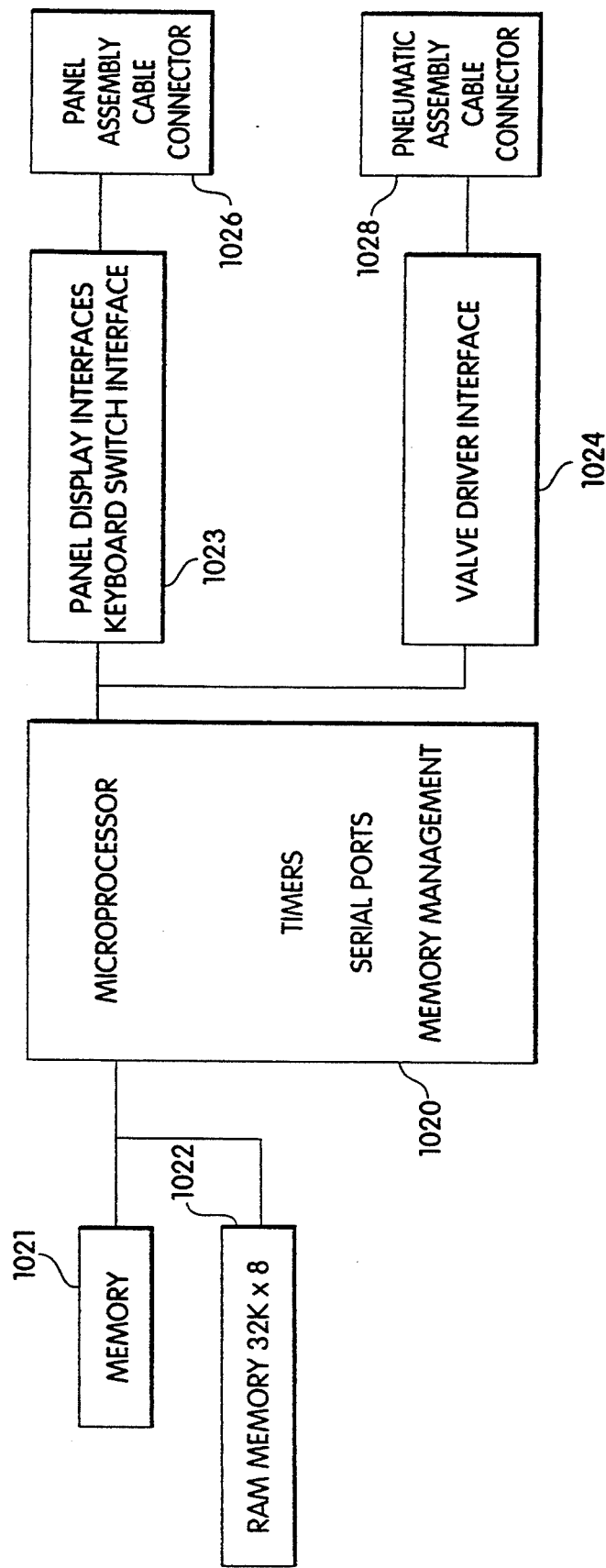
FIGS. 11(a) and 11(b) are schematics of the electronic controller and associated circuitry of the present invention.
Figure 11B:
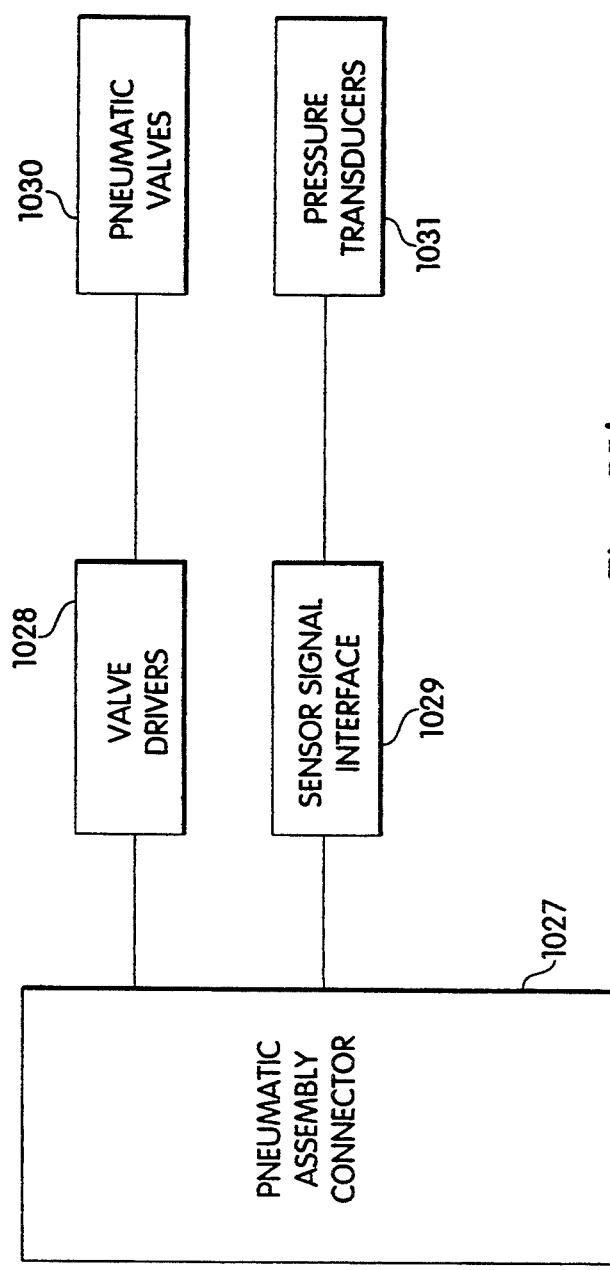

As described above, the present system illustrated in FIG. 11(*a*) contains a microprocessor 1020 or other electronic controller to control the sequencing of operations in the blood processing unit of the present invention. The electronic controller may have a program contained in a suitable device (disk, ROM, etc.) to control the functioning of various of the operations of the present invention. Record data may be contained in a memory device such as RAM memory 1022 in FIG. 11(*a*). A panel display and keyboard interface 1023 provides the human interface to operation of the system. A valve driver interface provides controls for the operation of the pneumatic system which controls the pneumatic valves and pumps of the present invention. A pneumatic assembly cable connector 1025 provides a pneumatic connection from the permanent subsystem to the disposable subsystem. A panel assembly cable connector 1026 provides an electrical connection within the permanent subsystem. Turning now to FIG. 11(*b*), FIG. 11(*b*) illustrates a pneumatic assembly connector 1027 which is in communication with connector 1025 of FIG. 11(*a*). Valve driver 1028 will operate the various pneumatic valves 1030 disclosed above in the present invention. Pressures sensed by the pressure transducers 1031 are received by a sensor signal interface device 1029 known to those skilled in the art and forwarded through pneumatic assembly connector 1027 to the microprocessor 1020 for actuation of the system as described above.

Figure 12A:
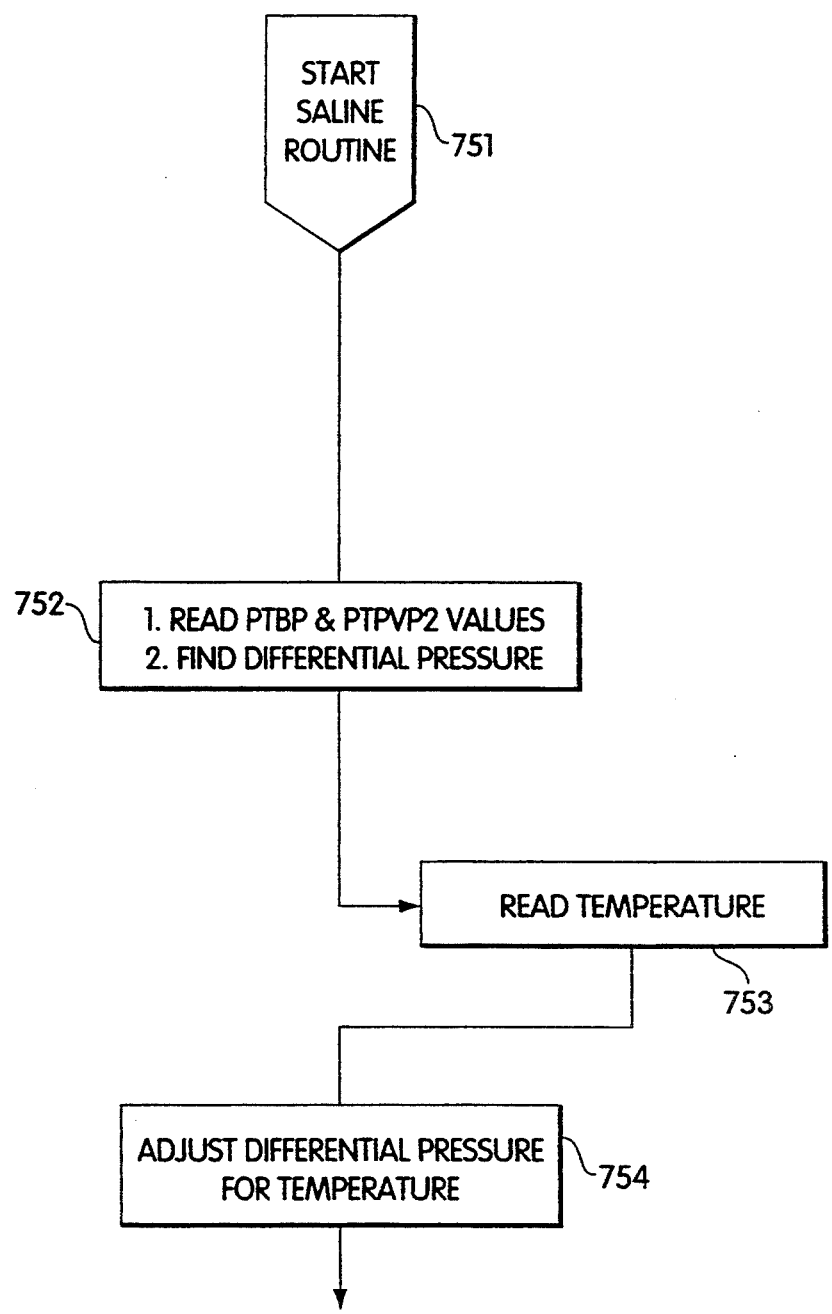
FIGS. 12(a) and (b) are flow diagrams illustrating the functioning of the saline control program of the present invention.
Figure 12:
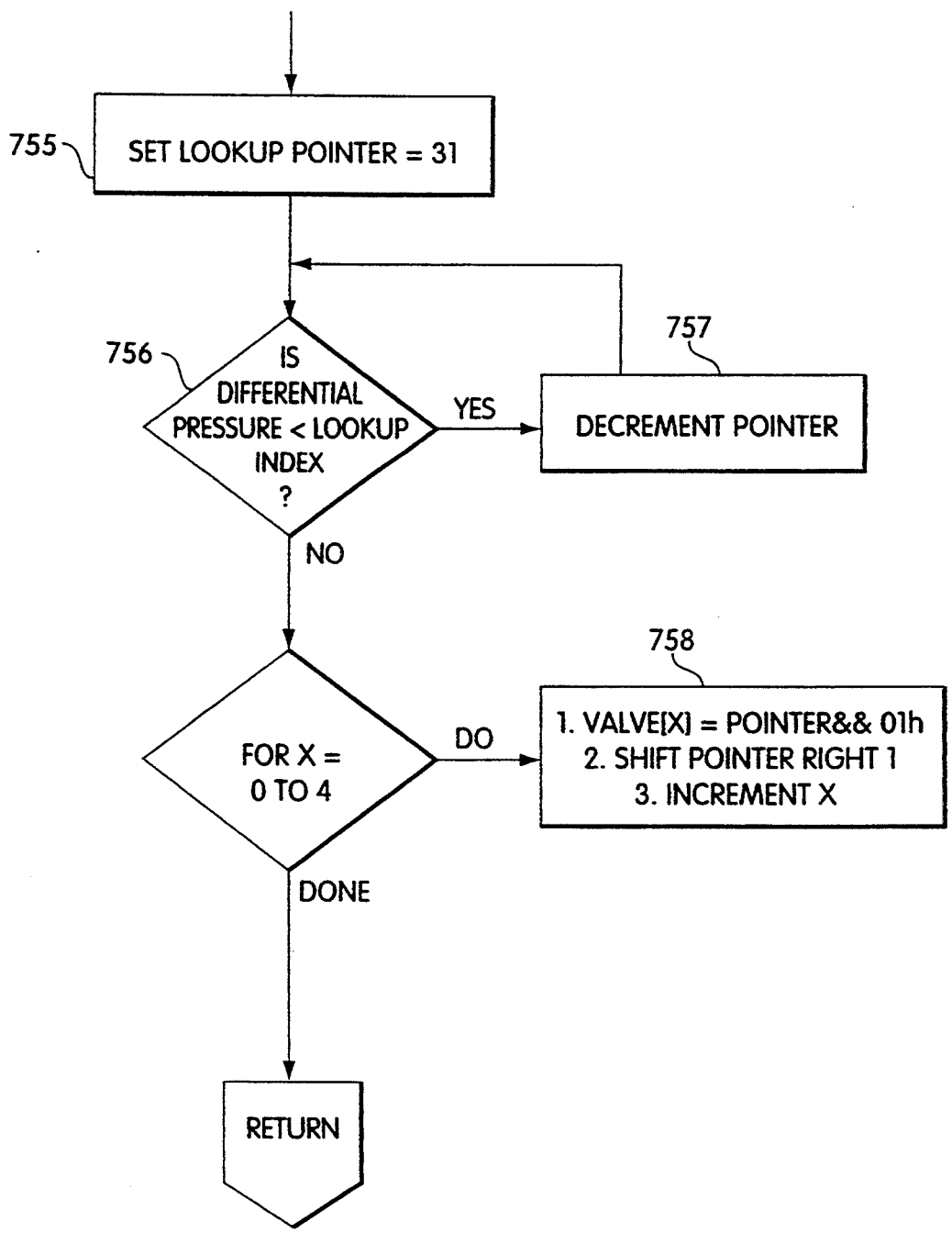

For example, the introduction of wash fluid into the system during operation may be contained in a set of instructions which are processed by the microcontroller to measure the hematocrit value of the blood and add wash fluid as required or desired, as explained above. FIG. 12 illustrates a flow chart containing a set of instructions acted upon by the microprocessor. In a first step 751, the saline control routine begins, initiated by the electrical control system. The system may sense a differential in pressure after blood passes through the first filter or, as desired, the routine may be always in an active mode of operation. The routine may also be activated by a manual control. Regardless of the method of initiation, in the next step 752, the program controller will cause the respective pressure transducers to read the pressure at the blood pump and upon the blood exiting the first tangential filter. The differential between the two pressures is then calculated in step 752. In step 753 the temperature of the blood is taken by an appropriate sensor (not shown) in communication with the blood line. As explained above, the temperature of the blood will affect the viscosity of the blood and thus the differential pressure drop, if any, across the first tangential filter. The temperature measured is sent to the microcontroller 1020 of FIG. 11(a) and, in step 754, the differential pressure is adjusted for the temperature. In step 754, the look-up pointer of FIG. 8(e) is set to Entry 31, corresponding to the maximum opening of valves, as can be seen by reference to FIG. 8(d). In steps 757 and 758, if the pressure differential of step 754 is less than the maximum pressure differential sensed (181 mm.), then the pointer will be decremented entry by entry until the appropriate pressure differential is reached. When the appropriate differential is reached, in step 758 the microcontroller will cause the appropriate number of solenoids to open according to the scheme of FIG. 8(d). This action, as explained above, will cause an appropriate amount of wash fluid to be introduced in the blood line. In lieu of steps 755,756 and 757, once the pressure differential has been determined, the look-up table of FIG. 8(d) will be accessed for a match, and the appropriate valves opened. In addition, it will be understood that in the embodiment of FIG. 9 using a pulse width modulated valve, in step 758 the valve would be opened for a duration corresponding to the appropriate entry in FIG. 8(e), the duration of opening corresponding to the settings x through 31× of FIG. 8(d) or a setting based on an equation which provides the same relationship of duty cycle to the differential pressure in the separator(s).

An accumulator 169, for example, a diaphragm accumulator as illustrated, may alternatively be used to store some of the blood exiting the main pump 124 so as to provide extra capacity to handle very high blood flow rates as can periodically occur during an operation. Also, between the pumping of each batch of blood by the main pump 124, that is, during those periods when the main pump 124 is not stroking, a relatively constant velocity flow can be maintained through the tangential separator 136 by using pressurized gas from a gas pressure source 171, all as seen in FIG. 2. Similar accumulators 173 and 175 can be used, respectively, for the anticoagulant and the washing fluid, using respectively, the gas pressure sources 177 and 179. Note that all gas pressure sources may connect to a single pump or source as may all vacuum sources.

The use of a diaphragm pump is particularly advantageous since such a pump does only minimal damage to any red cells and platelets being pumped by it and it is simple and inexpensive whereby it can be a disposable unit, e.g., made out of clear plastic. A disposable pump has the advantage that it does not contain viruses, bacteria, etc., from previous use. It is convenient to have both the washing fluid pump 162 and the anticoagulant pump 168 also be diaphragm pumps since this makes coordinated operation very easy (using pneumatic actuation) along with metering of the amount of anticoagulant being supplied to the blood being recovered from the wound, the amount of anticoagulant being proportional to the amount of blood being pumped by the main pump 124. Similarly, the amount of washing fluid being pumped by the washing fluid pump 162 is proportional to the amount of fluid being pumped by the main pump 124 whereby a proper amount of washing fluid is supplied.

In accordance with an embodiment of the invention the diaphragm 74 of the main pump 124 (and generally the diaphragms of the washing fluid pump 162 and the anticoagulant pump 168, when such are present) is sealed at its periphery 93 to the internal wall structure defining the chamber 102 and is of a shape and size sufficient to fit, without being stretched or expanded, substantially matingly against the internal wall structure defining, along with the appropriate side of the diaphragm 74, each of the subchambers 104 and 26. Thus, the diaphragm 74 does not need to elastomerically stretch and does not need to elastomerically expand on pressurization of the pressurization chamber 104, but does need to flex during its movement. The material of the diaphragm 74 can be flexible plastic (e.g., plasticized vinyl), elastomeric (e.g., polyurethane, silicone rubber) or whatever is desired, so long as it satisfies the above listed requirements and does not deleteriously affect the blood cells or platelets.

FIG. 2 also shows use of an optional microemboli filter 78 prior to reintroduction of The resuspended red blood cells into the patient. A flexible blood bag 80 will generally be present so as to provide a relatively constant pressure head and to control the rate of introduction of the resuspended blood cells and platelets into the patient. This bag may be removed from the system after it is filled with blood in order to return blood to the patient.

FIG. 2 shows a tangential separator 136 for use in certain embodiments of the present invention and which differs from the tangential flow separator 36 of FIG. 1. The tangential flow separator 136 has a tubular membrane 140, which may be generally coaxial with the outer wall of the tangential flow separator 136, and through which plasma and particulate matter smaller than red cells and platelets will pass but through which red cells and platelets will not pass so long as flow is taking place. For example, the pores though the membrane 140 can be smaller than about 5 microns, the approximate diameter of a red cell (and of a platelet). Pores large enough to allow red cell and platelet passage can also be used with the flow rate preventing such passage.

In the embodiment of FIG. 2 washing fluid is not added through a membrane. Washing fluid may be, but is not necessarily, added upstream of (e.g., via line 181) and/or in the center of the tangential flow separator 136

(e.g., via line 183), all as illustrated. If it is not added the separator 136 merely removes plasma and small debris. This provides a concentrated red cell and platelet solution in which the cells and platelets can be washed more efficiently or can be returned to the patient without washing. If additional fluid is desired, washing fluid can be added downstream of separator 136 (e.g., via line 185).

If desired, an additional separator 236 can be downstream of the separator 136. The additional separator 236 can be of the nature of either the separator 36 or the separator 136 and may be accommodated in the same housing or structure as separator 136. The passage 150 can be a plurality of passages in, for example, a bundle of hollow cylindrical fibers having porous membrane walls or can be a plurality of flat passages made from membrane sheets. Appropriate valves 99, as illustrated in FIG. 2, can control and direct the needed flows.

The addition of wash fluid via line 183, or via line 185 if separator 236 is also used, has the major benefit of achieving dilution after fluid removal such that subsequent fluid removal eliminates more of the original fluid in the blood entering separator 136. This permits less washing fluid to be used for the same percent reduction in original blood fluid compared to the amount needed when introduced at the entrance to separator 136.

The wash fluid pump 162 of FIG. 2 may also be additionally connected to the defoaming and coarse filtering unit 11 of FIG. 2. The purpose of connecting the wash fluid pump to the filtering unit 11 is to allow for both priming and purging of the blood reservoir and plasma separators respectively, to be presently described.

Figure 13:
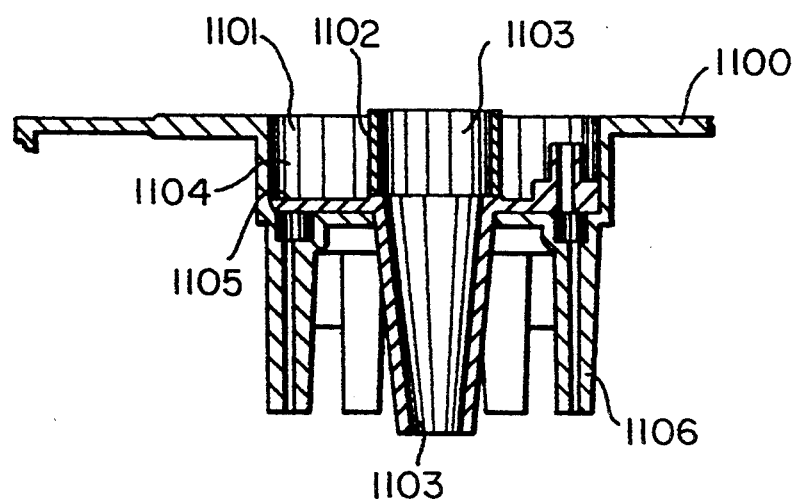
FIG. 13 is a drawing of a distributor apparatus for controlling the flow of wash or saline solution.

A saline solution prime of the system is desirable to wet the reservoir and a coarse filtering unit which includes a defoamer 12 and a filter 20. In addition, it may be desirable to prime the remaining parts of the system to remove air as well as to remove any chemicals from the system prior to processing of blood. For example, the separator 36 of FIG. 1 may be required to be primed for saline prior to its effective use. In addition, a chemical such as glycerine may be present in the plasma separator if the separator is comprised of hydrophobic membrane materials, as explained above. This glycerine must be removed prior to the flow of blood through the separator(s) to avoid infusion of glycerine into the patient upon reinfusion of blood. In operation, a line connection is made between the pump 162 through tubing to the coarse filtering unit 11. This tubing is filled with saline from saline pump 62 which is pumped through the coarse filter. In operation, once the user of the system apparatus of the present invention has completed the preliminary steps of connecting saline solution bags 60 as shown in FIG. 1 and a switch is activated, a pneumatically operated check valve is opened to allow saline solution to be pumped from the saline pump 162 to an access port shown to be on the top of the coarse filter 12. Saline is dispersed around the periphery of the filter by a distributor port shown in FIG. 13. The distributor port 1100 performs rapid and even wetting of the coarse filter 20. Turning now to FIG. 13, the distributor port 1100 has an upper annular cuplike portion 1101 and an inner wall portion 1102. The inner wall portion provides a separation from the annular portion and has depending therefrom a tubular member 1103. The annular portion has a bottom annular portion 1104 and a number of holes formed in the bottom portion around the periphery of the inner wall portion 1102. The holes 1105 lead to downwardly depending tubes 1106 in communication with holes 1105. The purpose of the tubes 1103 and 1006 is as follows. The distributor port is mounted in a position, as viewed in FIG. 2, just above and before member 12. During prime and purge with saline fluid as described above, saline will be introduced into the annular cuplike portion 1101 and will flow through holes 1105 and through tubes 1106. It is to be understood that the coarse filter 20 of FIG. 2 will be disposed surrounding or downstream from the distributor 1100. By means of the tubes 1106, saline will be spread uniformly around and evenly wet the filter material of filter 20. During blood processing operations, the tube 1103 will receive the blood suctioned from the patient site and allow blood to flow directly through to the filter 20, bypassing the tubes 1106. If desired, blood as well could be directed to flow through tubes 1106.

As saline is pumped by pump 162 into the reservoir 12, the reservoir fills up until such time the pumping chambers (26 in FIG. 1 and 102 of FIG. 2) are completely filled. When completely filled, the ball valve 34 will move to its raised position, as previously described, closing the port 32. The main diaphragm pump will then be activated, thereby dispersing saline throughout the system. This process may be repeated one or more times to assure full saturation with saline. Thus, the system will be primed with saline and the tangential flow separators will have their glycerine removed from their walls. Excess prime solution is collected in a waste fluid container 201 shown in FIG. 2 or out of outlet 64 of FIG. 1.

Once the system has been primed with the saline, blood processing is actuated, and blood will be drawn through wand 116 into the first filter body 11. Blood will then pass through the first coarse filter 20 and then go to the pumping chamber 102. At this point, blood will be present in pumping chamber 102 only, the remainder of the system still being filled with saline. It is desirable that the returned blood container 80 of FIG. 2 not contain an excess of saline solution. Thus, a scheme must be utilized which will remove the excess saline from the system prior to its introduction into the container 80 while preventing the flow of filtered blood also into the waste fluid container 201 shown in FIG. 2. This is accomplished during the startup of blood processing by opening a pneumatically actuated check valve such as a valve of a type shown in FIG. 8(b) which allows excess saline to flow into the waste fluid container. The flow of saline solution to the waste fluid container continues until the hematocrit level of the blood combined with the saline is of a desired level. Utilizing the hematocrit detection method described above, the pressure drop between the outlet of the first tangential separator 136 and the main pump pressure is continuously monitored. Initially, the pressure drop across the separator will be small, since little blood will be contained in the saline prime solution. The pressure drop will increase as more blood mixes with the prime saline solution. Once the hematocrit level has been reached, indicating that the hematocrit is of a selected and desirable level, the above-mentioned check valve will close and filtered blood will proceed to the blood bag 80 to be reinfused into the patient. Thus, by the method just described, the saline solution has been used to both wet the coarse filter to prime the system to remove glycerine from the plasma separator(s) will be removed from the system, and further prevents the solution from reaching the blood bag 80. By monitoring the hematocrit level of the blood and saline solution coming into the first plasma separator 136 there is a minimal loss of blood to the waste fluid container 201. At all times, the desired hematocrit level of the blood will be controlled for the introduction of only blood of the desired hematocrit level into the blood bag 80.

At the end of blood processing, which may coincide with the completion of the operative procedure, with little or no blood left remaining in the operative field, the amount of blood to be removed from the patient decreases significantly or ceases. There will be an amount of blood containing red blood cells remaining in the coarse filter 20, some blood remaining in the main pump 102, blood remaining in the lines leading through and to the separator(s) and blood and platelets in the separators. In order that the maximum amount of blood removed from the patient be filtered and processed and the system purged of blood, the saline pump 162 is once again utilized. At the end of blood processing, saline pump 162 pumps saline solution into the blood reservoir 11 through the distributor port shown in FIG. 13. The saline solution scavenges the remainder of blood cells which may be trapped in filter 20 and carries them to pump housing 102. The saline/blood solution then proceeds through the system, also pushing before it blood in the lines from the blood pump to the plasma separators 136 and 236. The plasma separators 136 and 236, as noted, themselves will contain amounts of blood cells which have not been flushed out and sent to the blood bag 80. A problem exists, similar to that on initiation of the apparatus, that while it is desirable to scavenge as many of the blood cells as possible, it is also desirable to keep the blood hematocrit level at the desired range so as not to unduly dilute the blood in blood bag 80. Were a predetermined fixed amount of saline solution to be flushed through the system at the end of blood processing, there is a good possibility that a large amount of saline infused into the blood bag 80 would upset the desired hematocrit level of the solution in blood bag 80.

Thus, once again using the pressure drop technique for measuring hematocrit discussed above, the control apparatus of the present invention will continuously measure the hematocrit level by the pressure drop across the separator 136. Once the hematocrit detector has determined that the hematocrit level is below a specified desired amount, thus indicating that an excessive level of saline solution mixed with blood, the control of the present invention will stop the pumping of the blood/saline solution through the system and to the blood bag 80. This function can best be seen with reference to FIG. 9 which is schematic of the electric controls of the present invention. If desired, when the lowest acceptable hematocrit levels are detected, the saline and waste pump are disabled and the blood pump is actuated for one final stroke at an accelerated flow rate to remove any trapped cells on the fiber walls of the tangential separators 136 and 236 and pump them to the blood bag.

As can be appreciated from the foregoing, the saline reservoir and saline pump is used for a number of purposes including priming the apparatus, maintaining the desired hematocrit level and purging the apparatus to remove the maximum amount of blood cells for reinfusion into the patient. Therefore, the control and metering of saline solution into the apparatus must be closely controlled. If the saline reservoir were to be emptied before, during or after processing, the entry of air into the system might affect its operation. In addition, the emptying of the saline bag 60 and the pumping of air through the system could lead to the pumping of air into the blood transfer bag which might be reinfused into the patient. To prevent this, the saline pump may be equipped with a check valve which is of identical design to the check valve 34 for the main blood pump that is shown in FIG. 2. During operation of the system, the absence of a full pumping chamber of pump 162, indicating an empty saline bag, would cause the operation of the entire system to be disabled. The same fill test method used to determine if there is blood in the blood pump is used to determine if there is saline in the saline pump. Upon replenishment of the saline solution, thus causing the saline pump to become full, the check valve to move to its closing position, the system would once again be activated and thus automatically continuing processing.

Figure 4:
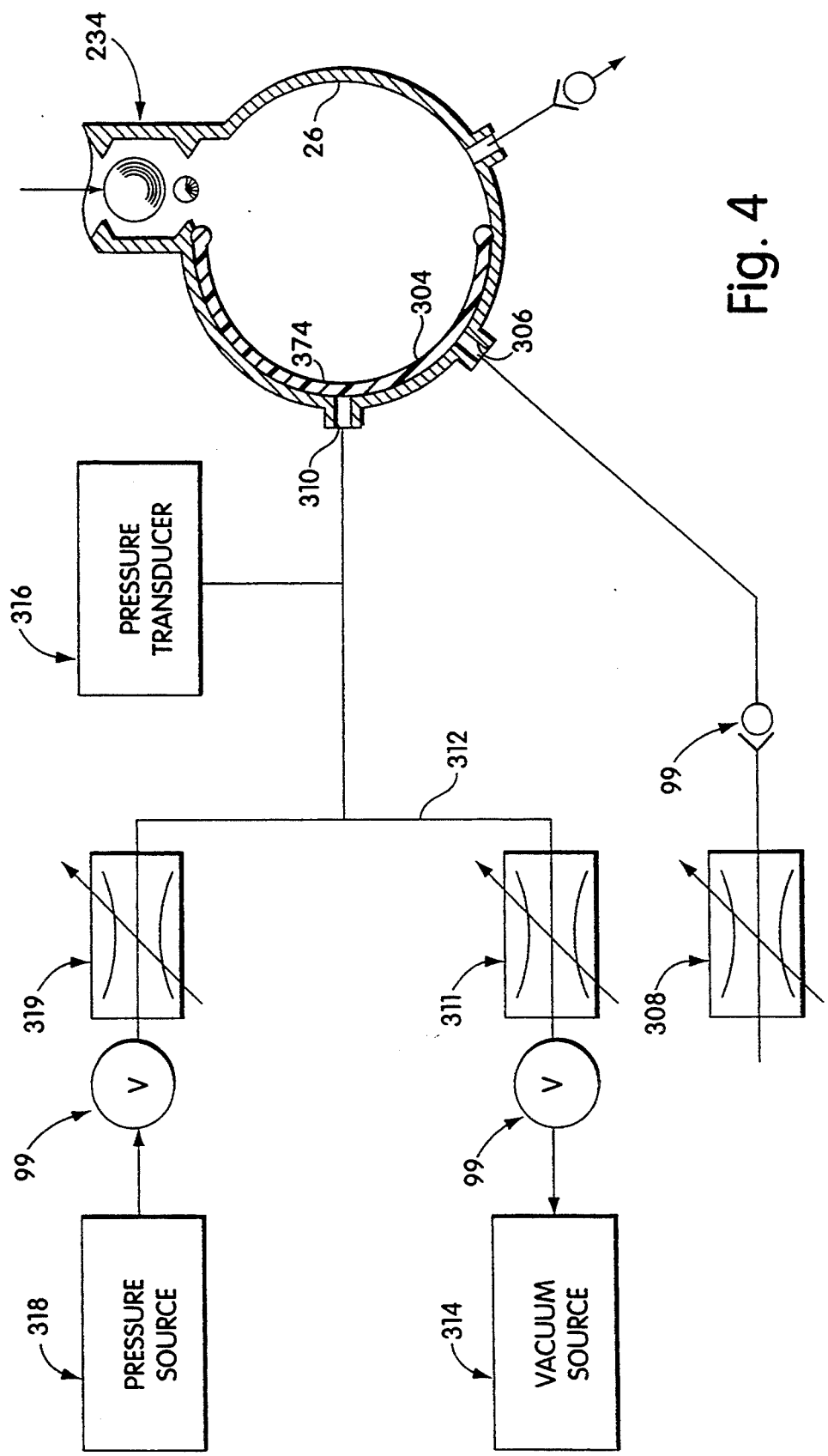
FIG. 4 illustrates, schematically, an alternate embodiment of a portion of an apparatus in accordance with the present invention.
Figure 5:
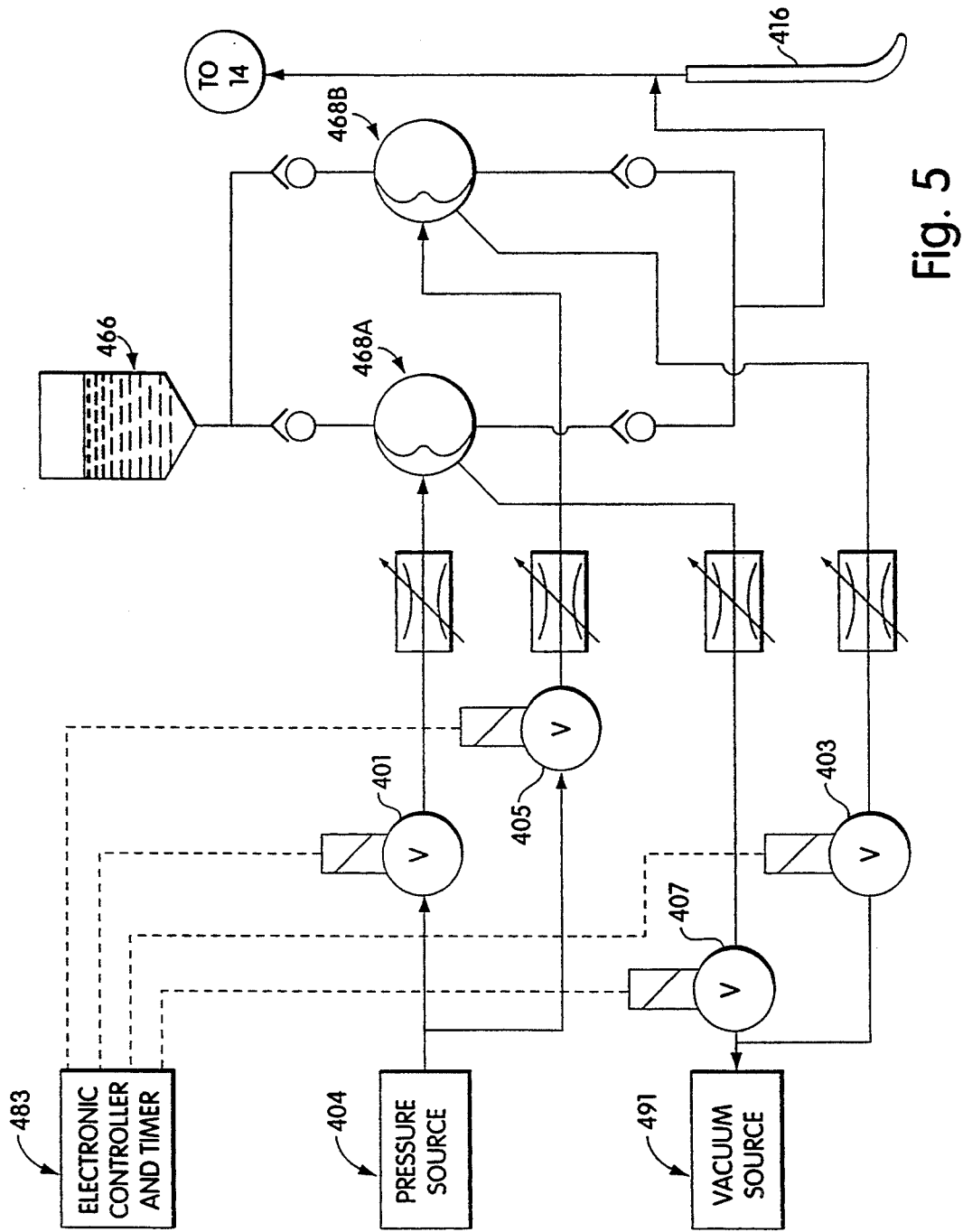
FIG. 5 illustrates, schematically, another alternate embodiment of a portion of an apparatus in accordance with the present invention.

FIG. 4 illustrates an alternate method for sensing when the pumping subchamber 26 is full. In the embodiment of FIG. 4 any one-way valve 234 may be used as the check valve 234, that is, it is not necessarily a float valve. The pressurization subchamber 304 has an opening 306 which communicates with the atmosphere, for example via an orifice 308 which limits flow. When the diaphragm 374 blocks the entry 310,306 or both, air cannot flow inwardly through the opening 306 into the pressurization subchamber 304 and from thence into a tube 312 via flow control valve or orifice 311. As a result, the pressure in the tube 312 drops towards that generated by the vacuum source 314. A pressure transducer 316 measures pressure in the tube 312 and when it reaches a (low) pressure threshold this activates introduction of pressurized gas for a preselected period of time from a pressurized gas source 318 via an orifice 319 into the pressurization subchamber 304. The orifice 308 limits outward flow sufficiently so that the diaphragm can eject all of the blood from the pumping subchamber 26 or a one-way valve 99 can be used to prevent gas flow out of opening 306 when 304 is pressurized. When blood is being sucked by the suction wand 16 it is desired to mix this flow of blood with a continuous flow of anticoagulant in the desired ratio of anticoagulant to blood. An embodiment of the present invention as shown in FIG. 5 can be used to accomplish this. Two gas-activated diaphragm pumps 468A,468B are used to pump anticoagulant. These pumps alternate anticoagulant ejection to provide constant or near-constant flow. The filing and ejection times for these pumps, from anticoagulant source 466, are then necessarily about equal. The total duration of two pump ejections substantially equals the complete cycle time (ejection plus filling) of a batch by the main pump (not shown in FIG. 5). The initiation of anticoagulant pump ejection occurs when the main pump ejects. Whenever the main pump ejects, each of the anticoagulant pumps 468A,468B eject a single time each, one after the other. Then, when blood is pumped the anticoagulant pumps 468A,468B produce continuous anticoagulant flow. Pumping of the anticoagulant pump 468A is initiated simultaneously with initiation of blood pumping by the main pump. This is accomplished under the control of electronic controller and time 483. Initially solenoid valves 403 and 407 are open and 401 and 405 are closed. When the main pump starts its stroke valve 407 closes and valve 401 opens. When anticoagulant pump 468A is emptied, at time, $t_1$, then electronic controller and timer 483 closes valve 401, opens valve 407, closes valve 403 and opens valve 405. AT time, $t_2$, when pump 468B is emptied, the valves revert back to their initial condition. At the time $t_2$, the main pump has completed a full stroking cycle (has delivered a batch of blood and been refilled) and if full is ready to stroke again. Total blood pumping flow rate by the main pump (the average of the amount pumped during stroking and zero flow during filling) is approximately equal to the blood suction rate at the suction wand 416 as fixed by wand design and vacuum level. This can work better than adding the accumulator 173 of FIG. 2 in providing a constant ratio of anticoagulant to blood during blood pumping.

In accordance with an autotransfusion method of the present invention a mixture of healthy blood cells, platelets, fluid, particulate matter and entrapped gases is recovered from a patient. The mixture is defoamed to remove the entrapped gases and is filtered to remove at least a portion of the particulate matter. The resulting filtered mixture enters the pumping chamber 26 of the main pump 24 and, after the pumping chamber 26 is full, is pumped out of the main pumping chamber 26 under pressure. Flow is prevented from occurring from the pumping chamber 26 back into the filtration apparatus. Flow is allowed from the filtering apparatus to the pump inlet port whenever the filtered mixture is not being pumped out of the pump outlet port 30. The filtered mixture is pumped through a narrow passage 50,150 in the tangential flow separator 36,136 or 236, either between a pair of membranes 38,40, or along the membrane 140, as the case may be, the passage 50,150 being no more than about 500 microns in height. The filtered mixture from the pumping chamber 26 or 126 is delivered to the passage 50,150 at a pressure in the passage 50,150 sufficient to expel blood fluid and small debris through the membrane 40 or 140 and at a flow rate through the passage 50,150 sufficient to prevent the blood cells from blocking or passing through the porous membrane 40 or 140.

In the case when the separator 36 is used, washing fluid is flowed across the narrow flow through passage 50. Blood fluid and washing fluid are removed from the outfacing surface of the second membrane 40. Pressure differentials are maintained across the membranes of the magnitudes previously set forth. In the case when separator 136 is used along or in conjunction with one or more additional separators 236, washing fluid is either not added or is mixed with blood fluid before, within or after separator 136 or at any combination of these locations.

As discussed above, the diaphragm pump as disclosed in the present invention provides a non-traumatic apparatus for moving blood to be processed. Similarly, were there to be excessive pressure within the apparatus, either in the blood lines carrying blood from the main pump through the plasma separators or from the plasma separators to the reinfusion bag 80 of FIG. 2, such excessive pressure could cause the various lines or the blood or waste bags to burst, clearly an undesirable result. It is desirable to prevent such excessive pressure, which may be due to a number of causes, such as clogging of the system for some reason or due to the clamping of a blood line or the closing of a blood line by an improperly operated pneumatic valve. The pressure drop measured across the separator 136 is once again utilized to determine presence of excessive pressure. It has been found that during normal blood processing the typical pressure drop across the separator 136 lies between 30 mm of Hg and 100 mm of Hg. If there were a clog, an improperly operated pneumatic valve or an inadvertently clamped blood line, the pressure drop across the separator 136 would be negligible while the blood pump actuation pressure would exceed its normal operating values which are in the range of greater than 300 mm of Hg. Detection of these out of range values signals the controller of the present invention to automatically disable the processing of blood within the system, such that blood is not damaged, and signal the system user of such occurrence.

Figure 15:
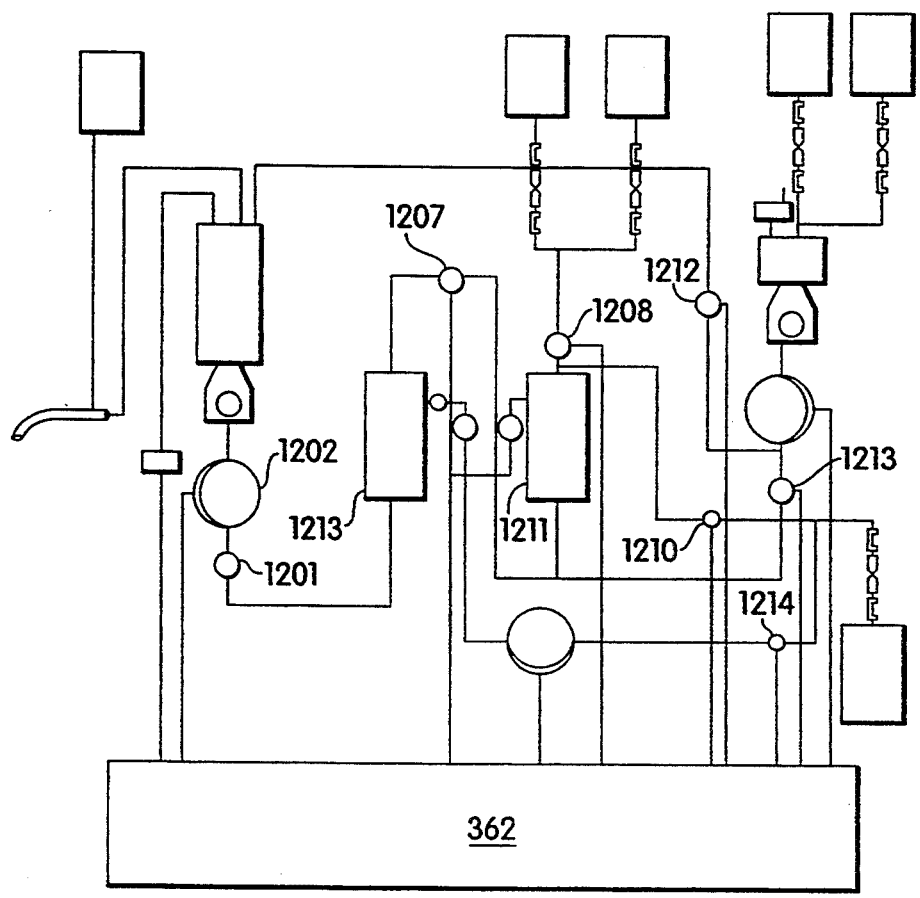
FIG. 15 is a schematic diagram illustrating the location and operation of pressure transducers and pneumatic valves used in the present invention.

While in the foregoing discussion, the operation of the pneumatic valve 306 was described in reference to the first separator, various other pneumatic valves may be used with the present invention. FIG. 15 illustrates in a schematic form the system of the present invention, with particular reference to the pneumatic valves incorporated therein. Pneumatic valve 1201 controls, through an on/off action, the flow of blood from the blood pump 1202 to the remainder of the system of the present invention. Pneumatic valve 1207 in a similar manner controls the flow of blood after the first separator 1213. Pneumatic valve 1208 in a similar manner controls the flow of blood before entering the blood bag 1209 and is used, for example, in preventing the flow of saline into the blood bag prematurely, as described herein. Pneumatic valve 1210 is located at the line exiting the second separator 1211 and is used during startup of the system to dump saline which has been used to prime the system into the waste bag to prevent its infusion into the blood bag 1209. Pneumatic valve 1212 is connected to the wash or saline bag and pump and is used in manner similar to valve 1207 to control the flow of saline to the coarse filter for purposes explained above of prime and purge. Pneumatic valves 1213 and 1214 in a similar manner control, respectively, the outputs of the saline pump and the waste pump. In addition, the controller shown in FIGS. 10, 11(a) and 11(b) performs certain monitoring functions including self-diagnostic testing by electronics, self-diagnostic testing on pneumatic components and checking for correct attachment of the disposable processor module onto the reusable actuator. Thus, the controller will: (1) monitor pressure thresholds and limits with pneumatic lines (2) monitor hematocrit levels for delivery of saline as discussed above, pinpoint potential failures, such as the saline solution bag being empty, monitor and display the amount of blood collected for processing, as well as the amount of blood processed and display system status through appropriate audible and/or visual alarms. In addition to the normal on and off functions of the controller to begin and stop processing, in a preferred embodiment two different levels of processing are provided. In the first, a standard blood processing mode, blood will be processed at approximately 250 ml per minute. This has been shown by experience to achieve a plasma removal efficiency of approximately 90%. In another mode, the ortho mode, blood flow is limited to 150 ml per minute out of the blood reservoir due to the slower rate of processing and a higher proportion of saline wash is used, which results in plasma removal efficiency of approximately 96%. The actuator module of FIG. 12 may have appropriate controls by which the operator can engage the standard or the ortho mode. At the slower ortho flow rate, a larger amount of saline wash fluid is added to the blood processing cycle in order to increase the washing efficiency of the collected blood. The additional saline fluid dilutes the blood further and allows more fluid and waste to be removed by the separators. The ortho made is provided since orthopaedic shed blood tends to have more blood damage and contamination by tissue, debris, fat and bone chips than most other types of surgically shed blood and requires additional wash fluid to adequately obtain an acceptable processed blood product. In addition, a PURGE mode button or control may be provided to, as disclosed above, purge the red blood cells out of the processor and into the blood bag. Finally, a PAUSE mode control may be provided for collecting blood in the reservoir without processing it. Finally, a PRIME control mode may be activated to remove air and infuse saline through the system to remove glycerine from the plasma separators as disclosed above before blood processing begins.

Figure 16A:
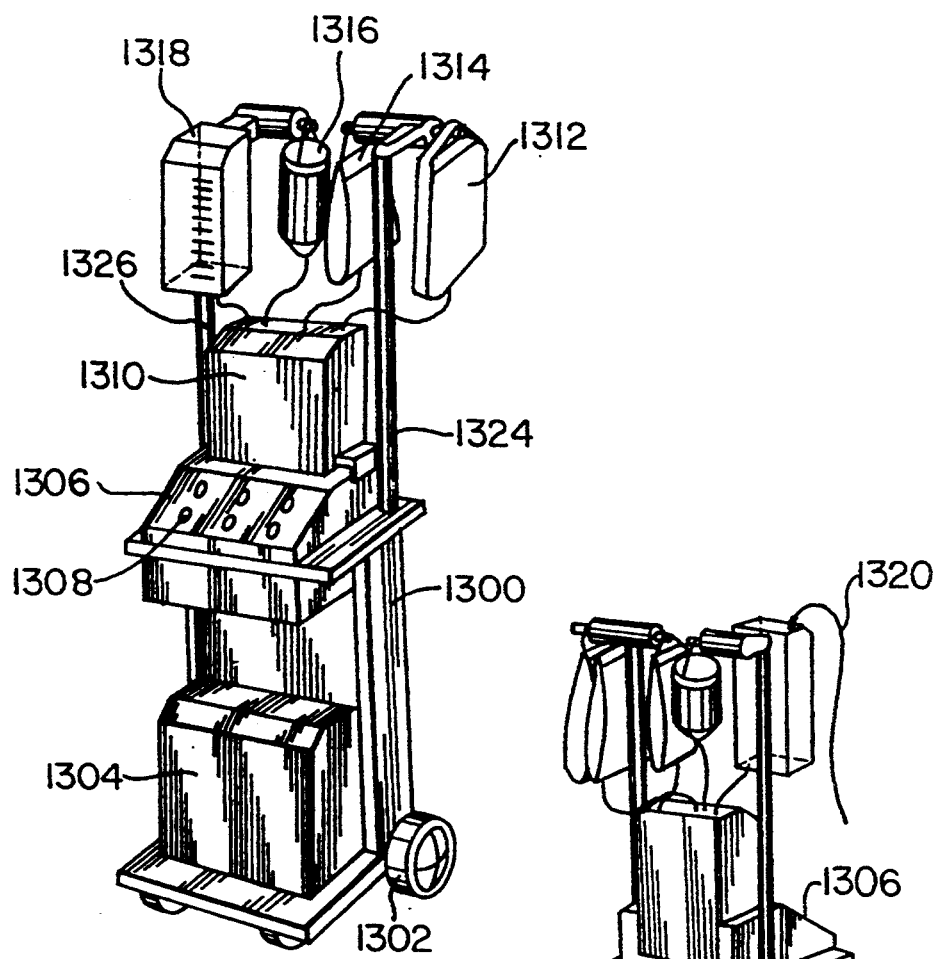
FIGS. 16(a) and (b) illustrate the assembly housing incorporating the structure of the apparatus of the present invention.
Figure 16B:
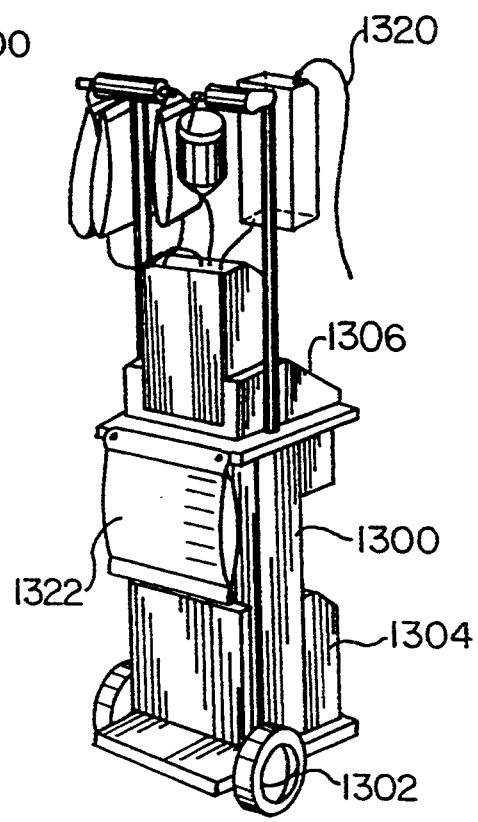

Turning now to FIGS. 16(a) and 16(b), those figures illustrate an assembly housing for the components of the present invention illustrated schematically in FIG. 10. The assembly housing, designated as 1300, is a generally upright support which may incorporate wheels 1302 to ease movement of the assembly around the operating room. A compartment 1304, shown in the drawing at the lowermost level of the housing, may contain the various electrical supply components, as well as the source of pneumatic and vacuum supply for operating the various pumps and solenoids contained in the present invention and described above, the microprocessor and its related memory and control software, and generally the electrical portions of the apparatus of the present invention.

Located just above the compartment 1304 is another compartment 1306. The compartment 1306 is in electrical and pneumatic connection with compartment 1304 and forms the interface between the permanent, non-replaceable portions of the present invention and the disposable portions of the present invention, illustrated in FIG. 10 as a disposable portion 361 and a permanent portion 362. The compartment 1306 may also serve as a control panel and contain a number of switches 1308 for controlling the apparatus of the present invention in a conventional manner. The compartment 1306 may contain all or some of the electrical control components (such as the computer controls) instead of being located in the lower compartment 1304.

The disposable portions illustrated in FIG. 10 as reference numeral 361 comprise those portions of the apparatus which are disposable and thus of single use, as explained above with reference to FIG. 10. As shown in FIG. 16, the disposable portions are contained within a single housing or cartridge 1310, which may be fitted into the portion 1306, where the various pneumatic and other contacts described above will be made. The lower portion of the disposable cartridge which mates with the upper portion of the compartment 1306 may have suitable conventional guiding or mating surfaces (not shown) to assist in proper alignment of the cartridge on the portion 1306 and proper alignment of pneumatic or other contacts. Once a blood processing routine is completed, the disposable cartridge will be removed and discarded.

The embodiment of FIG. 16 illustrates that the processor of the present invention consists of three main portions or sections: (a) a reusable actuator which contains the electromechanical, electronic and pneumatic components necessary to operator the blood processor; (b) a disposable blood processor which is comprised of the fluid lines, blood, wash and waste pumps, the separators, and various connecting lines to the reusable actuator; and, (c) a precollection blood reservoir into which blood is collected prior to connection to the disposable blood processor for processing. As shown in FIG. 16, various of the disposables and supplies may be external of the assembly housing 1300. For example, the container 1312 may be used to receive blood which has been processed through the apparatus of the present invention. Anticoagulant may be contained in a bag 1314 and saline solution in a bag 1316. The blood reservoir for blood to be processed may be located internally of the housing or cartridge 1310 or externally, as shown by precollector 1318, as will be explained in further detail below. If the precollector 1318 is located externally of the cartridge, the precollector may have attached thereto a suction tube and associated wand 1320 for purposes of suctioning blood from an operative site for delivery to a reservoir within the cartridge 1310. If there is no separate precollector, the suction tube and associated wand may be connected directly to the cartridge. The blood processor may be of 3000 ml. in capacity and the blood reservoir in the blood processor itself reduced in volume capacity to approximately 250 ml. due to the use of the precollector to serve as the main receptacle for blood to be processed.

Waste materials from blood processing operations are collected in waste bag 1322 where they may be disposed. As shown in FIG. 16(a), the disposables may be supported on extension poles 1324 and 1326 to locate the bags above the cartridge 1310. These poles may be extendable as desired as in conventional IV poles.

Figure 17B:
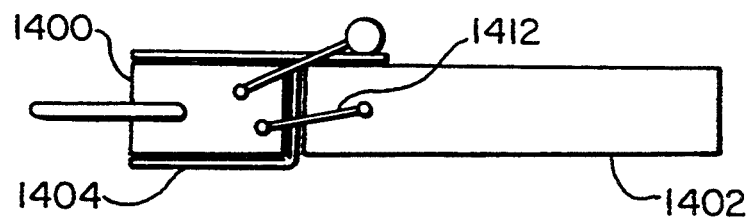
FIGS. 17(a) and (b) illustrate another embodiment of the present invention in which the filtering unit is incorporated as a separate precollection unit.
Figure 17A:
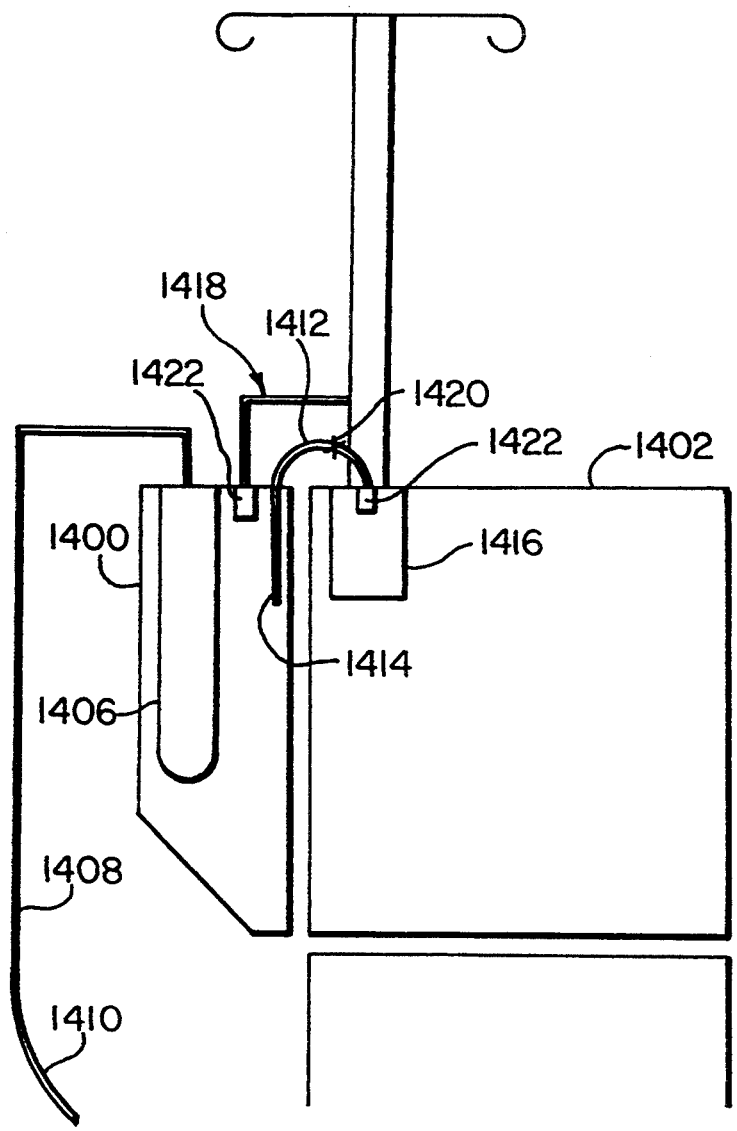

FIGS. 17(a) and (b) are schematic illustrations of a variation of the arrangement of the precollector and processor cartridge of FIG. 16, in which the precollector 1400 is designed to mate with and cooperate with the processor cartridge 1402. As shown in FIG. 17(b), the precollector is supported in close proximity to the cartridge 1402 by a support structure 1404. The precollector 1400 may contain a defoamer and 20 micron pore size filter assembly 1406 which is attached to a suction tubing 1408 and suction wand 1410. Because the precollector is removable from the cartridge, the precollector may be used remotely from the remainder of the blood processing apparatus of the present invention and serve as a cardiotomy reservoir until it is attached to the cartridge and its contents removed as will be described below. This may be convenient when the blood processing apparatus of the present is located outside the operating room environment. In addition, the precollector may be used separately when only a "rough" filtering is required or when time does not permit processing through the apparatus. In addition, the precollector may be used separately when an insufficient amount of blood (for example, less than 900-1000 ml.) to justify use of the blood processor, due in this case to the expense of the blood processor. In this event, the filtered and defoamed blood from the precollector may be transferred to a transfer reinfusion bag. Thus, the precollector has the dual purposes of "standalone" operation and operation in conjunction with the blood processor of the present invention. The use of a precollector which is separate from the processor yet cooperates with it has the advantage that the processor is not used when there is an insufficient amount of blood aspirated to justify its use. Sometimes, it is unclear at the beginning of a procedure of the amount of blood which will be shed. Without a separate connecting precollector, the more expensive blood processor with internal receptacle would be used regardless of the amount of blood aspirated from the operative site. The precollector may be used already attached to the cartridge and the apparatus of the present invention in a manner to be described below.

A blood transfer line 1412 is shown in FIG. 17(a) and (b) as being attached to a tube 1414 which extends into the precollector 1400 to allow for the contents of the precollector to be suctioned into a blood reservoir 1416 within the cartridge 1402. A vacuum line 1418 is connected to a suitable source of vacuum to provide the suction for the suction wand 1410 to remove blood from the operative site, through the filter 1406 and into the precollector 1400. The transfer of blood from the precollector 1400 to the cartridge 1402 is permitted or inhibited by a pinch or other closure valve 1420 in the transfer line 1412. When the pinch or other closure valve 1420 is opened, blood within the precollector 1400 will enter the reservoir 1416 if the pressure in the cartridge containing the reservoir 1416 is lower than the pressure within the precollector 1400. This may be accomplished by either the use of separate vacuum sources for the reservoir 1416 and the precollector 1400 or by utilizing the cartridge's vacuum and limiting the transfer to situations in which blood is being suctioned from the operative site. In addition, the precollector may be simply mounted higher in level than the reservoir and the force of gravity used to move blood from the precollector to the reservoir. Vacuum protection float valves may be incorporated into each of the precollector and the reservoir to prevent the vacuum ports from being compromised by blood within either of the cavities when they become filled with blood during a blood suctioning procedure.

If the precollector is to be used always with the reservoir within the cartridge of the apparatus of the present invention, the filter and defoamers shown in FIG. 2 may be moved directly into the precollector, which would allow for the cartridge to be made smaller and thus less expensive. Such arrangement would also allow for the precollector to be used remote from the apparatus of the present invention as desired, with their joining to be made a a time after the blood has been collected. As well, if blood loss is rapid and reinfusion of processed blood needed as soon as possible, the two units, that is, the precollector and the cartridge, may be used together such that blood in removed from the operative site and immediately processed for reinfusion. Blood entering the precollector passes through the defoamer and filter assembly. Once a sufficient amount of blood has been collected in the precollector to justify using the blood processor, the user connects the precollector to the blood processor through blood transfer line 1412. Prior to passing blood through the blood processor, however, the blood processor is washed and primed with sterile saline fluid, as described herein, to remove residual glycerine and air from the system to the waste bag. The precollector, upon insertion into the support bracket 1404, may trip or close a suitable electrical switch to inform the microprocessor controlling the operation of the apparatus of the present invention that the precollector is in place and the system is ready for processing operations.

Figure 18:
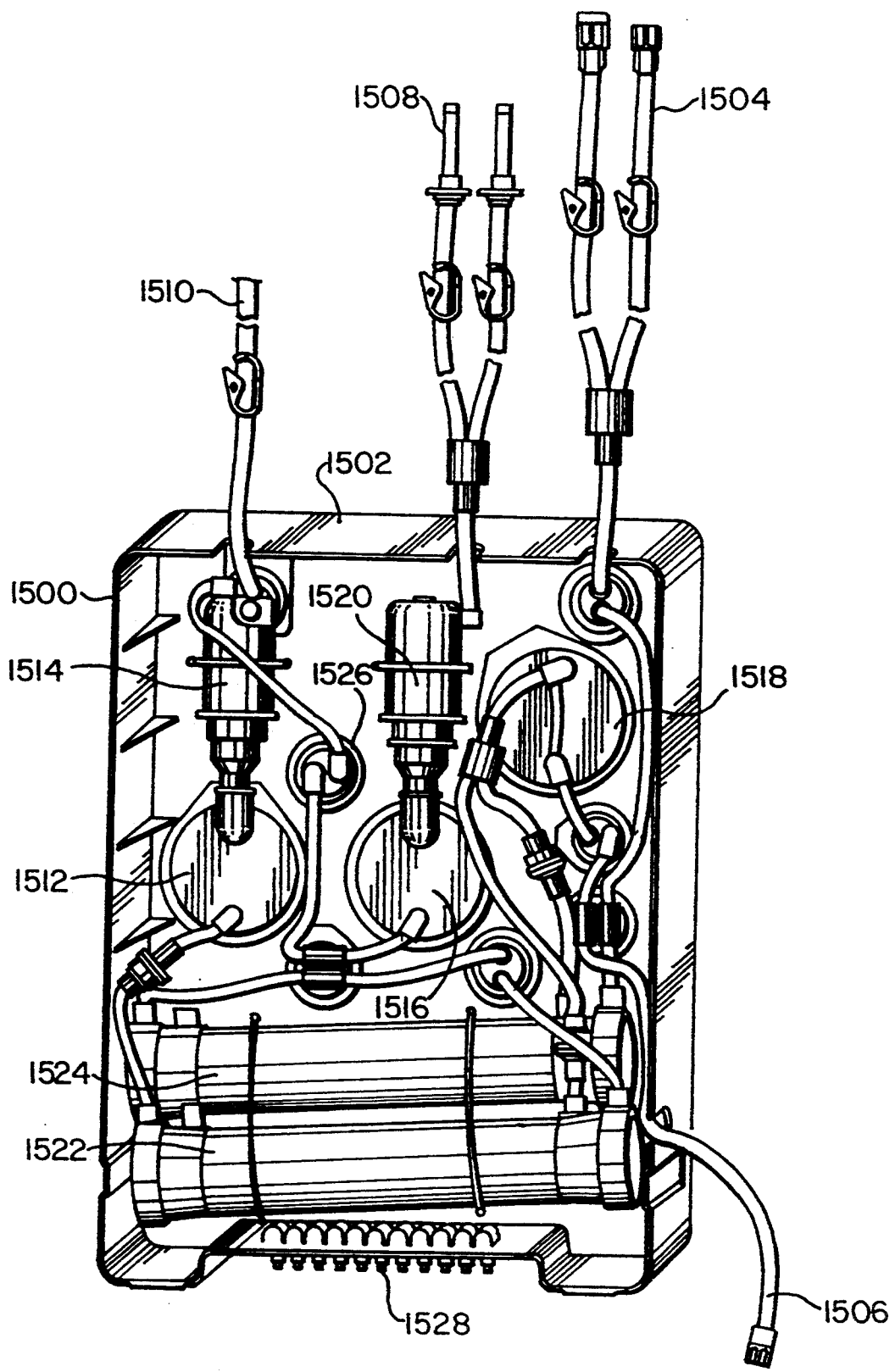
FIG. 18 illustrates an embodiment of a disposable blood processing unit of the present invention.

FIG. 18 illustrates an embodiment of the disposable blood processor illustrated in FIG. 16 as reference numeral 1310. The disposable unit of FIG. 18 illustrates a compact disposable unit 1500 which may be fitted into the unit 1306 of FIGS. 16(a) and (b). Unit 1500 may be constructed of any material suitable for disposal, such as a plastic material, and consists of a main housing 1502. Fixed within the tray-like housing 1502 are contained the components illustrated in FIGS. 1 and 2: a blood bag collection line 1504 which receives the output of the blood processed from the blood processor; a waste line 1506 which conveys waste fluids from the blood processor; a line 1508 which is designed to receive a source of saline wash fluid for purposes discussed above; an inlet line 1510 which is connected to a source of blood to be processed, such as a precollector 1400 illustrated in FIGS. 17(a) and (b); a blood pump 1512 which receives blood from line 1510 through blood reservoir 1514; a saline pump 1516 and associated reservoir 1520 for the purposes discussed herein; a waste pump 1518 which pumps waste fluids through to line 1506, as described herein; first and second separators 1522 and 1524 to separate blood products as described in detail herein; one or more pneumatic valves, such as 1526, for purposes detailed herein; and connectors 1528 which form one end of the pneumatic and vacuum lines within the housing 1502. These connectors 1528 will mate with and connect to a number of corresponding connectors contained with the reusable housing (1306 in FIGS. 16(a) and (b)). These connections allow the controlled operation of the disposable blood processing portion of the present invention. It can be seen that disposable compact unit, after use in a blood processing operation, may be disconnected from the precollector, blood bag and waste bags, removed from the reusable unit 1306 and disposed. The disposable unit 1500 also includes indentations 1530 and 1532, which serve to interconnect the disposable unit 1500 with the reusable portion of the device of the present invention.

Figure 19:
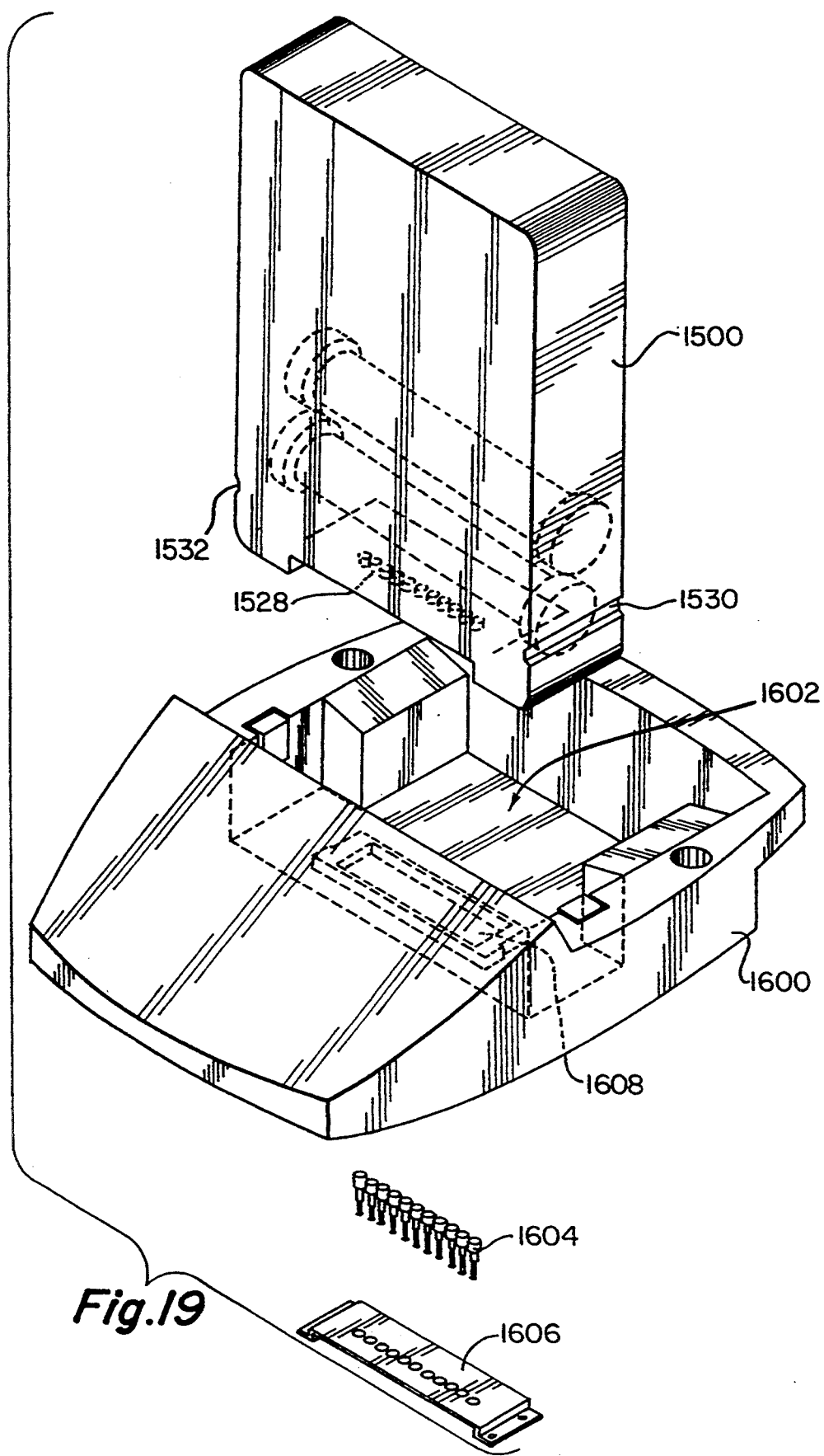
FIG. 19 illustrates a preferred embodiment for the interconnection of the disposable blood processor with the reusable housing.

FIG. 19 illustrates the disposable unit 1500 and its interconnection with the reusable portion 1600. The reusable portion 1600 shown in FIG. 19 is similiar in form and function to portion 1306 in FIGS. 16(a) and (b). Indentations 1530 and 1532 on the disposable unit 1500 will mate with spring or other biased detents (not shown) within the open housing 1602 into which the unit 1500 is received. Connectors 1528 formed on the disposable unit 1500 will connect with corresponding connectors contined within the housing 1600. Corresponding connectors 1604 are mounted on plate 1606, and the assembly mounted within the bottom hole 1608 formed in the open housing 1602. The connectors 1604 within housing 1600 are connected to sources of vacuum and pneumatic pressure, for the purposes explained herein. The connectors 1528 and 1600 matingly engage such that each of the individual connectors will engage a corresponding connector upon insertion of the disposable unit 1500 into the unit 1600. The connectors 1528 may engage with the connectors 1600 with male/female frictional couplings (not shown).

Figure 20A:
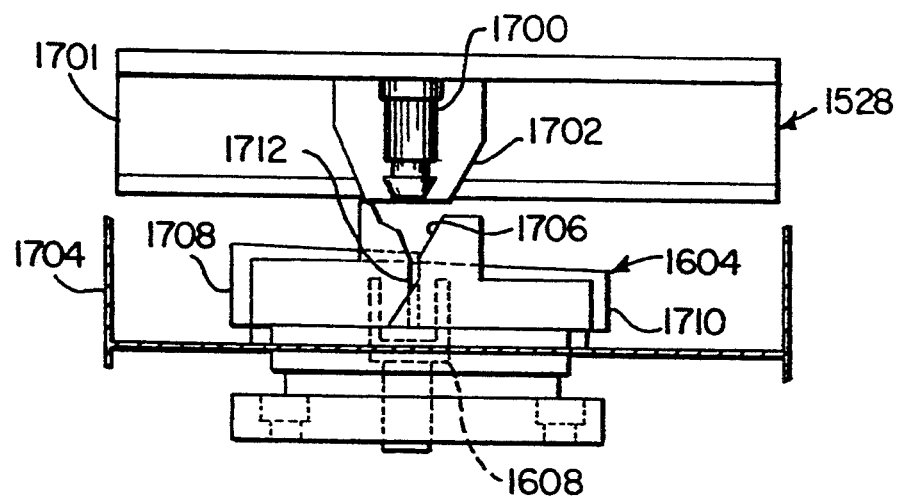
FIG. 20(a) and (b) illustrates a camming device for use in connection with the embodiment of FIG. 19.
Figure 20B:
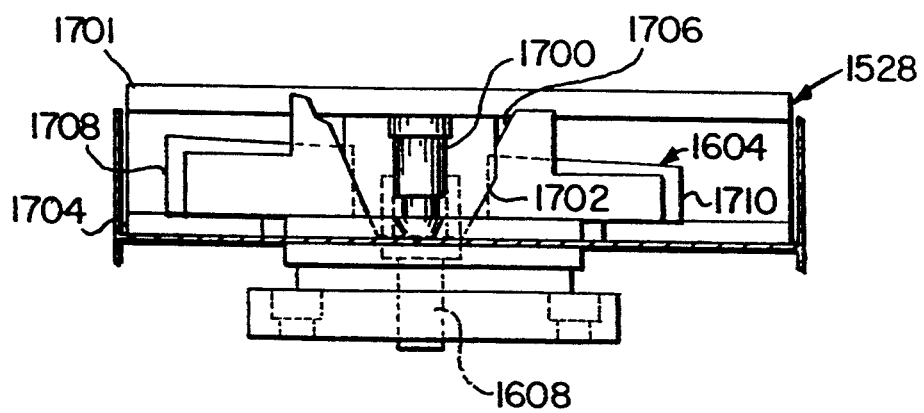

FIGS. 20(a) and (b) illustrate in some detail a side view of the interconnection of the connectors 1528 to connectors 1604 when the disposable unit 1500 is inserted into the open housing 1602. A housing 1701 has formed at its ends a sloped or cammed portion 1702. The housing 1704 containing connectors 1604 contains a corresponding cammed or sloped surface 1706 which is biased (by means not shown) to the position of FIG. 20(a). Plates 1708 and 1710 are attached to cammed surface 1706 and in FIG. 20(a) form a closed surface (with suitable gasket material 1712) to seal the openings in connectors 1604 so that dirt and fluid do not contaminate or otherwise compromise the connectors 1604. As shown in FIG. 20(b), when the unit 1500 is inserted into the opening 1602 of FIG. 19, the cammed surface 1702 will engage the cammed surface 1706 and cause plates 1708 and 1710 to move away from one another, exposing connectors 1608 and permitting the interconnection of connectors 1528 with connectors 1604.

Industrial Applicability

The present invention provides a blood pumping and processing system 10 which has embodiments which can be used for intraoperative autotransfusion, plasmapheresis, hemodialysis, hemoconcentration and other therapeutic and/or diagnostic blood treatment applications. This system can provide blood filtration, plasma separation, metered anticoagulant delivery and metered washing fluid delivery for plasma removal and replacement.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A blood processing system for use in processing blood of various hematocrit levels aspirated from a surgical site comprising:
    a separator for receiving the aspirated blood and for separating a mixture of blood cells and platelets from blood fluids;
    means for conveying the blood being processed through the blood processing system; and,
    means for controlling the hematocrit level of the reinfused blood cells and platelets which comprises:
        means for measuring a first pressure of blood entering the separator;
        means for measuring a second pressure of blood existing the separator;
        means for measuring the difference between the first and second pressures; and
        means, responsive to the measured pressure differential, for adjusting the hematocrit of the mixture of blood cells and platelets.

2. The blood processing system of claim 1 wherein the means for adjusting the hematocrit of the mixture is a means for infusing wash fluid into the mixture.

3. The blood processing system of claim 2 wherein the means for measuring pressure comprises pressure transducers.

4. The blood processing system of claim 1 wherein the means for measuring and adjusting are controlled by a programmed microprocessor.

5. A blood filtration unit having a container for receiving blood aspirated from an operative site, an inlet opening into the container for conveying the aspirated blood into the container, a filter within the container for filtering blood received from the operative site, the filter being in communication with the inlet opening such that blood aspirated from the operative site first enters the inlet opening and subsequently the filter, the container further having a storage portion to store filtered blood, wherein the improvement comprises:
    the inlet opening being a distributor cap having a central aperture for conveying blood from the operative site into the container, the distributor having disposed around the central aperture a plurality of distributing apertures, the distributing apertures having a means for connection to a source of wash solution, the distributing openings being adapted to convey wash solution entering through the means for connection into the filter to wet the filter prior to the entry of aspirated blood and to dislodge cellular blood materials from the filter and into the storage portion of the container.

6. The blood filtration unit of claim 5 wherein the plurality of distributing apertures surrounds the central aperture to uniformly wet the filter and dislodge blood materials from the filter.

7. A system for blood storage and processing purposes comprising:
    a disposable housing for processing blood received in the housing;
    a reservoir contained within the disposable housing for receiving blood from outside the housing and having an opening therein for communication with a source of blood;
    a precollector having a housing, the housing having an inlet which may be connected to a means for suctioning blood and other fluids from an operative site;
    the inlet communicating with a filter to filter blood introduced through the inlet, wherein blood passes through the filter and into the precollector housing for storage purposes or for purposes of transfer into the reservoir;
    a support housing associated with the disposable housing, the support supporting the precollector;
    an inlet on the precollector for receiving a vacuum line to withdraw filtered blood contained in the precollector;
    a blood transfer line contained partially within the precollector to provide a conduit for withdrawal of the filtered blood and partially outside the precollector to communicate with the opening in the reservoir to allow the withdrawal of blood from the precollector into the reservoir and disposable housing.

8. The system of claim 7, wherein the filtered blood is moved from the precollector to the reservoir through the action of a vacuum source connected to the inlet on the precollector.

9. The system of claim 8 further comprising a float valve connected to the inlet to prevent the ingress of blood into the vacuum line from the precollector.

10. A blood processing system for use in processing aspirated blood in which blood fluids are separated comprising:
    a disposable housing for processing blood received within the housing;
    the disposable housing having a separator for receiving the aspirated blood and for separating a mixture of blood cells and platelets from blood fluids;
    the disposable housing further having means for conveying blood to the separator for separating blood cells;
    a reusable housing which cooperates with the disposable housing;
    the reusable housing having means for controlling the means for conveying blood for separating blood cells from blood fluids wherein the reusable housing cooperates with the disposable housing through at least one connector which mates with a corresponding connector in the disposable housing.

11. The blood processing system of claim 10 in which the means for controlling the separating of blood cells is under the control of a programmed controller.

12. The blood processing system of claim 11 in which the programmed controller comprises a microprocessor controlled and associated control program.

13. A blood processing system for use in processing blood of various hematocrit levels aspirated from a surgical site comprising:
 a separator for receiving the aspirated blood and for separating a mixture of blood cells and platelets from blood fluids;
 a transducer for sensing a first pressure of blood entering the separator;
 a transducer for sensing a second pressure of blood exiting the separator;
 a microprocessor for determining the difference between the first and second pressures; and
 a pump controlled by the microprocessor for introducing a variable amount of fluid into the mixture of separated blood cells and platelets, the pump delivering a variable amount of fluid in response to the pressure differential determined by the microprocessor so as to adjust the hematocrit of the mixture of blood cells and platelets.

14. The blood processing system recited in claim 13 further including a pump for pumping blood to be processed into the separator wherein the transducer for sensing the first pressure is in communication with the pump.

15. The blood processing system recited in claim 13 wherein the separator and the fluid pump are supported by a disposable housing and the microprocessor and the transducers for sensing the first and second pressures are supported by a reusable housing.

16. The blood processing system recited in claim 13 wherein the separator includes an outlet and the system further includes a pneumatically controlled diaphragm valve which is in communication with the outlet of the separator and the transducer for sensing the second pressure.

17. The blood processing system recited in claim 16 wherein the pneumatically controlled diaphragm valve includes first and second ports in communication with one side of the diaphragm and a third port on an other side of the diaphragm, wherein the first and second ports regulate fluid flow through the valve and the third port conducts positive or negative pressure relative to the diaphragm.

18. The blood processing system of claim 13 wherein the fluid pump includes a driving chamber and a pumping chamber and wherein a valve admits a variable volume of media into the driving chamber to cause a variable amount of fluid to be pumped from the pumping chamber.

19. The blood processing system recited in claim 18 wherein the valve includes multiple solenoid switches.

20. The blood processing system recited in claim 18 wherein the valve includes a pulse width modulated valve.

21. A blood processing system for use in processing aspirated blood in which blood fluids are separated comprising;
 a disposable housing for processing blood received within the housing;
 the disposable housing having a separator for receiving the aspirated blood and for separating a mixture of blood cells and platelets from blood fluids;
 the disposable housing further including a pump for conveying blood to the separator for separating blood cells;
 a reusable housing which cooperates with the disposable housing having at least one pneumatic connector which mates with a corresponding connector in the disposable housing and including a microprocessor for controlling the pneumatic pressure applied to the pump.

22. The blood processing system recited in claim 21 wherein the disposable housing includes a plurality of collinear pneumatic connectors.

23. The blood processing system recited in claim 22 wherein the reusable housing includes a plurality of mateable collinear pneumatic connectors.

24. The blood processing system recited in claim 21 wherein one of the disposable housing and the reusable housing includes a camming member and the other includes a cover moveable between a first position when the pneumatic connectors are sealed by the cover and a second position when the pneumatic connectors are unsealed, the cover including a receiving portion against which movement of the camming member will move the cover from the first position to the second position.

25. The blood processing system recited in claim 24 wherein the cover is resiliently biased into the first position.

26. A blood processing system, comprising:
 first and second separators for separating blood cell and fluid components, each separator having an inlet for the blood to be processed and an outlet for the separated blood cells and an outlet for the separating fluid, a line in communication with the blood cell outlet of the first separator and the inlet of the second separator;
 a blood pump for pumping the blood to be processed into the first separator;
 a fluid pump for introducing a variable amount of fluid into the line;
 a waste pump for pumping the separated fluid from the first and second separators;
 a plurality of pneumatic diaphragm valves for controlling the flow of blood and fluid through the blood processing system;
 a plurality of pneumatic connectors in communication with the plurality of pneumatic diaphragm valves; and
 a disposable housing for supporting the first and second separators, blood pump, fluid pump, waste pump, plurality of pneumatic diaphragm valves and plurality of pneumatic connectors.

27. The blood processing system of claim 26 wherein at least one of the blood pump, fluid pump and waste pump are pneumatically driven and the disposable housing includes corresponding pneumatic connectors in communication therewith.

28. A method of processing blood, comprising:
 introducing blood into a separator which separates the blood into cell components and blood fluids;
 determining a pressure differential between the blood introduced into the separator and the blood exiting the separator;
 introducing a predetermined variable amount of fluid into the separated blood cell components to adjust the hematocrit level to a desired amount in response to the determined pressure differential.

* * * * *